United States Patent [19]

Goodman et al.

[11] Patent Number: 5,011,828

[45] Date of Patent: Apr. 30, 1991

[54] IMMUNOSTIMULATING GUANINE DERIVATIVES, COMPOSITIONS AND METHODS

[76] Inventors: Michael Goodman, 6455 Calle de Lagrima, Rancho Santa Fe, Calif. 92067; William Weigle, 13750 Ruette Le Parc, Apt. C, Del Mar, Calif. 92014; Stanley Bell, 732 Braeburn La., Narberth, Pa. 19072; Robert Chen, 39 Beverly Dr., Belle Mead, N.J. 08502; Roland K. Robins, 3 Titan, Irvine, Calif. 92715; William J. Hennen, 2306 Long Dr., Bryan, Tex. 77802

[21] Appl. No.: 190,697

[22] Filed: May 5, 1988

Related U.S. Application Data

[63] Continuation-in-part of Ser. No. 798,629, Nov. 15, 1985, Pat. No. 4,746,651, which is a continuation-in-part of Ser. No. 546,679, Nov. 1, 1983, Pat. No. 4,643,992.

[51] Int. Cl.$^5$ .................. A61K 31/70; C08B 31/00
[52] U.S. Cl. ................................................ 514/45
[58] Field of Search ........................ 514/45; 536/24

[56] References Cited

PUBLICATIONS

Chem. Abst. 72: 55806j, 1970.
Chem. Abst. 106: 16903q, 1987.

*Primary Examiner*—John W. Rollins
*Attorney, Agent, or Firm*—Dressler, Goldsmith, Shore, Sutker & Milnamow, Ltd.

[57] ABSTRACT

7,8-Disubstituted guanosine nucleoside derivatives are found to be potent immune response enhancing agents in human and animal cells. 7-Substituents are hydrocarbyl radicals having a length greater than ethyl and less than about decyl. 8-Substituents are =O, =S, =Se and =NCN. Compositions and methods of use are also disclosed.

29 Claims, 6 Drawing Sheets

IN VITRO RECONSTITUTION OF PRIMARY HUMORAL IMMUNE RESPONSE TO SRBC BY 7o8oGuo IN IMMUNODEFICIENT CBA/N MICE

IMMUNOSTIMULATING GUANINE DERIVATIVES, COMPOSITIONS AND METHODS

CROSS-REFERENCE TO COPENDING APPLICATION

This is a continuation-in-part of copending application Ser. No. 798,629 filed Nov. 15, 1985 now U.S. Pat. No. 4,746,651 which was a continuation-in-part of application Ser. No. 546,679, filed Nov. 1, 1983, now U.S. Pat. No. 4,643,992.

TECHNICAL FIELD

The present invention relates to immune response enhancing compounds (immunostimulants), and more particularly to guanine nucleoside derivatives that are substituted at the 7- and 8-positions of the guanine ring, as well as to compositions containing those derivatives and methods of their use.

BACKGROUND OF THE INVENTION

An animal's immune system is comprised of numerous elements that act separately and/or in concert to counteract, to eliminate, or to neutralize substances that are recognized by that system as foreign to the animal host. Generally, but not necessarily, the substance recognized as foreign by the immune system has its origin exogenous to the host. Exemplary of such exogenous substances are infectious bacteria and the by-products of their cellular activity, virus particles and their proteins, proteins injected by insect stings, and the like. In autoimmune diseases, such as rheumatoid arthritis, the host's immune system recognizes host-made proteins or self-made proteins as foreign.

The principal effectors of the immune system are the leukocytes, which include lymphocytes of thymic origin (T cells), lymphocytes produced in bone marrow (B cells), neutrophils which, inter alia, produce enzymes that make oxidizing agents such as hydrogen peroxide that have cytotoxic effects upon bacteria, and macrophages which present the foreign substance or antigen to the T cells, as well as produce a protein designated interleukin-1 that assists T cell transformation into T helper cells. Complement which is a complex mixture of proteins that acts in an ordered, cascading manner upon the foreign substance also plays a major role in immune responses.

B cells can be distinguished from T cells, inter alia, by the presence of immunoglobulins on their membrane surfaces. The membrane-bound immunoglobulins function as antigen receptors; secreted immunoglobulins function as antibodies.

There are five known classes of immunoglobulins, identified as IgA, IgD, IgE, IgG, and IgM on the basis of five antigenically different heavy chain proteins which in part make up the immunoglobulin molecule. B cells also bear non-immunoglobulin cell markers, including a complement receptor (CR), a receptor for the Fc portion of immunoglobulin (FcR), I-region associated antigens (Ia), and a set of differentiation antigens (Lyb 1-7) which are identified by all antisera and are correlated with various aspects of B cell maturation and activation. These markers are useful in phenotypically identifying B cells.

While the B cell immunoglobulins interact with the foreign substance, or antigen, the T cells, and particularly helper T cells, are believed necessary to stimulate B cells to divide and to differentiate into antibody secreting cells for humoral immunity. Suppressor T cells contribute to the regulation of humoral immunity, while cytotoxic T cells and T cell mediators of delayed-type hypersensitivity are the principal effectors of cell mediated immunity.

T cells bear antigens designated Lyt 1, 2, and 3 as well as L3T4 that are related to T cell functions. Helper T cell precursors are of the Lyt $1^+$, $2^-$, $3^-$, L3T4$^+$ phenotype. It is these cells which normally participate in the activation and regulation of B cells.

Helper T cells are known to assist in activation and differentiation of immunoglobulin-secreting B cells after a first message is received by the B cells from the activating antigenic agent. However, the mode by which the T cells provide the second message of activation and differentiation to the B cells is not entirely understood currently.

Guanosine-3',5'-cyclic monophosphate (cGMP) has been implicated as a naturally occurring agent for providing the required second message for B cell proliferation. 8-Bromoguanosine-3',5'-cyclic monophosphate (8-BrcGMP) has been found to be a weak synthetic intracellular lymphocyte mitogen.

The immune response can be modified by artificial supression (immunosuppression) or enhancement (immunopotentiation or immunostimulation). Immunosuppression; i.e., artifically induced decreased responsiveness, can be achieved by six general methods: (1) blockade by antigen, (2) administration of specific antisera or antibody, (3) use of other biologic reagents such as antilymphocyte antisera, (4) use of drugs or hormones, (5) radiation, and (6) surgical removal of lymphoid tissue. Immunopotentiation can include the administration of an agent effecting an increase in the rate at which the immune response develops, an increase in the intensity or level of the response, a prolongation of the response, or the development of a response to an otherwise non-immunogenic substance.

The agents that are known to enhance immune responses are generally termed adjuvants and can be placed into two general classes: (1) those providing general potentiation; i.e., substances that enhance cellular and/or humoral immune responses for a wide variety of antigens, and (2) those providing specific potentiation, i.e., substances which enhance specific responses to certain antigens only.

Substances that can act as class-1 adjuvants can be grouped into the following categories: (1) water and oil emulsions, e.g., Freund's adjuvant, (2) synthetic polynucleotides, (3) hormones, drugs and cyclic nucleotides, (4) endotoxins, (5) proteinaceous lymphokines and monokines, e.g., interleukins.

An immunopotentiated state can be illustrated by the bodily condition after vaccination. Here, the immune response is already enhanced due to an antigenic response, but could be beneficially enhanced still further to provide an improved degree and/or duration of immunity.

Immunopotentiation can occur in animals that exhibit a normal immune response as well as in animals that exhibit a compromised immune response. In the latter situation, immunopotentiation is relative to the immunocompromised status of the host animal, and rather than enhancing the response to supernormal levels, a protective degree of immunity (i.e., nearly normal levels) is sought and is referred to as immuno-reconstitution. References to immunoenhancements hereinafter are to be understood to include immuno-reconstitution.

In some diseases and physiological conditions such as AIDS, X-linked agammaglobulinemias, senescence and drug-induced-immunosuppression, antigen-dependent B cell activation and differentiation is lacking and/or exists only at a reduced level, thereby lessening the humoral immune response of the host. These diseases and conditions are representative of immunosuppressed states. Here, enhanced activation and differentiation, if it can be effected, tends to beneficially lessen the disease manifestation and/or improve the patient's condition.

Co-assigned U.S. Pat. No. 4,539,205 to Goodman and Weigle describes modulation of animal cellular responses with 8-substituted guanine derivatives bonded 9-1' to an aldose having 5 or 6 carbon atoms in the aldose chain (ring). The cellular modulations described in that patent relate mostly to immunomodulation such as adjuvanticity in enhancing primary and secondary immune responses. Activity against certain neoplastic conditions is also disclosed as are T cell-replacing activity, an IL-1 like activity (assayed on thymocytes), and induction of the release of lysosomal enzymes from neutrophils. The 8-substituents in those molecules have electron withdrawing inductive effects relative to hydrogen. Thus, halo, mercapto or its thioxo tautomer, acyl mercapto, alkyl sulfido, nitro, cyano, keto, halomethyl and methyleneoxy alkyl and the like were disclosed as useful, while electron donating substituents such as an amino group were found to be inactive.

In addition, co-assigned U.S. Pat. No. 4,643,992 and its corresponding published European patent application No. 83306791.1 further disclose the use of derivatives of 8-hydroxyguanosine (8-oxoguanosine), 7-methyl-8-oxoguanosine and 7-methyl-8-thioxoguanosine in modulating animal cellular responses. Further results using guanine derivatives disclosed in U.S. Pat. No. 4,539,205 are also disclosed in U.S. Pat. No. 4,643,992, as are similar results using guanine derivatives disclosed for the first time in that patent.

Still further, several papers and book chapters have been published by some of the present inventors and their co-workers relating to still further effects of compounds disclosed and claimed in U.S. Pat. No. 4,643,992. Exemplary of those published papers are Goodman, *Proc. Soc. Exp. Biol. Med.*, 179:479 (1985); Goodman, *J. Immunol.*, 136:3335 (1986); Goodman and Weigle in *Purine Metabolism In Man, Part B*, Nyhan and Thompson, eds., Plenum Press, N.Y., page 451 and 443 (1986); Goodman and Weigle, *J. Immunol.*, 135:3284 (1985); Goodman and Wolfert, *Immunol. Res.*, 5:71 (1986); Goodman, *J. Immunol.*, 137:3753 (1986); and Goodman and Hennen, *Cell. Immunol.*, 102:395 (1986).

BRIEF SUMMARY OF THE INVENTION 7,8-Disubstituted guanine nucleosides (guanosine derivatives) are utilized to enhance an immune response in human and animal cells. A useful disubstituted guanine nucleoside has a structure that corresponds to the formula:

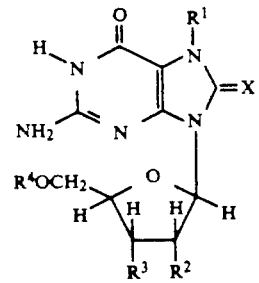

wherein X is O, S, Se or NCN; $R^1$ is a straight, cyclic or branch chain hydrocarbyl radical that has a length greater than an ethyl group (longer than two carbon atoms) and less than a decyl group (shorter than a ten carbon chain); $R^2$ and $R^3$ are the same or different radicals selected from the group consisting of hydrogen, hydroxyl, lower alkoxy, lower alkanoyloxy, and benzoxy groups, or $R^2$ and $R^3$ together constitute a lower alkylidenedioxy radical; and $R^4$ is selected from the group consisting of hydrogen, lower alkanoyl and benzoyl groups. Preferred guanosine derivatives of this invention are those in which X is O or S and $R^1$ has a length greater than ethyl and less than hexyl. Particularly preferred guanosine derivatives are 7-allyl-8-thioxoguanosine, 7-allyl-8-oxoguanosine, 7-butyl-8-oxoguanosine, 7-(2-butenyl)-8-oxoguanosine, 7-benzyl-8-oxoguanosine and 7-propyl-8-oxoguanosine. 7-Allyl-8-oxoguanosine is most preferred. The pharmaceutically acceptable, non-toxic base addition salts of the compounds of formula I are also contemplated.

An immune response-enhancing composition that contains a diluent amount of a physiologically tolerable carrier together with an immunopotentiating (or immunostimulating) effective amount of an above-described disubstituted guanine nucleoside derivative as an active ingredient is also contemplated by this invention.

A method of enhancing an immune response, and particularly an antigen-specific immune response is also contemplated. Here, leukocytes are contacted in an aqueous medium with a composition containing an immunostimulating amount of a before-described guanine nucleoside derivative. Contact between the composition and leukocytes is maintained for a time period sufficient for the contacted cells to manifest enhancement of their immune response. This method can be practiced in vivo or in vitro for cell cultures. The leukocytes contacted are preferably B lymphocytes.

A method for preparing an 8-oxo, 8-thioxo or 8-selenoxo purine substituted at the 7-position with an allyl or hydrocarbyl-substituted allyl group is also contemplated. In accordance with this method, a purine starting material is provided substituted at its 8-position by a group $—X—CH_2—CR=CH_2$, wherein X is S, O or Se and R is hydrogen, lower alkyl or benzyl, and substituted at its 9-position by a blocking group. The 8-substituted purine starting material is heated to a temperature of about 50° C. to about 200° C., preferably in a diluent, inert liquid medium. The temperature is maintained for a period of time sufficient (about one hour to about two weeks) for the purine starting material to form a purine product substituted (i) at the 8-position by the group $=X$, wherein X in the product is the same as X in the starting material, and (ii) at the 7-position by a group $—CH_2—CR=CH_2$. The reaction can also be catalyzed by the inclusion of a catalytic amount of PdCl$_2$ in the liquid medium. Preferably, the product is isolated. Preferably also, the purine is a nucleoside bonded 9-1' to a ribose or deoxyribose, and the purine product is a guanosine, adenosine or inosine derivative. Most preferably, that purine nucleoside is a guanosine derivative such as those discussed herein.

BRIEF DESCRIPTION OF THE DRAWINGS

In the drawings forming a portion of this disclosure.

Three groups of CBA/CaJ mice were utilized. Each group was immunized with the TNP-BSA conjugate. One group received the 100 percent sesame oil-guanosine derivative, a second group received the 2 percent sesame oil-guanosine derivative, and the third group (dashed line) received no guanosine derivative and served as a control.

Antibody titers to TNP-BSA were determined over a period of 37 days using standard enzyme-linked immunosorbent assay (ELISA) procedures with TNP-BSA as antigen. Data are shown as a ratio of the titer obtained using either guanosine-containing composition to the control titer. Thus, at 37 days post immunization, animals receiving the 7a8MGuo from the 100 percent sesame oil vehicle exhibited about 5-times the titer of the control animals, whereas animals receiving 7a8M-Guo from the 2 percent sesame oil vehicle exhibited about 4-times the titer of the control animals. Further details of these studies are discussed hereinafter.

Figure 5:
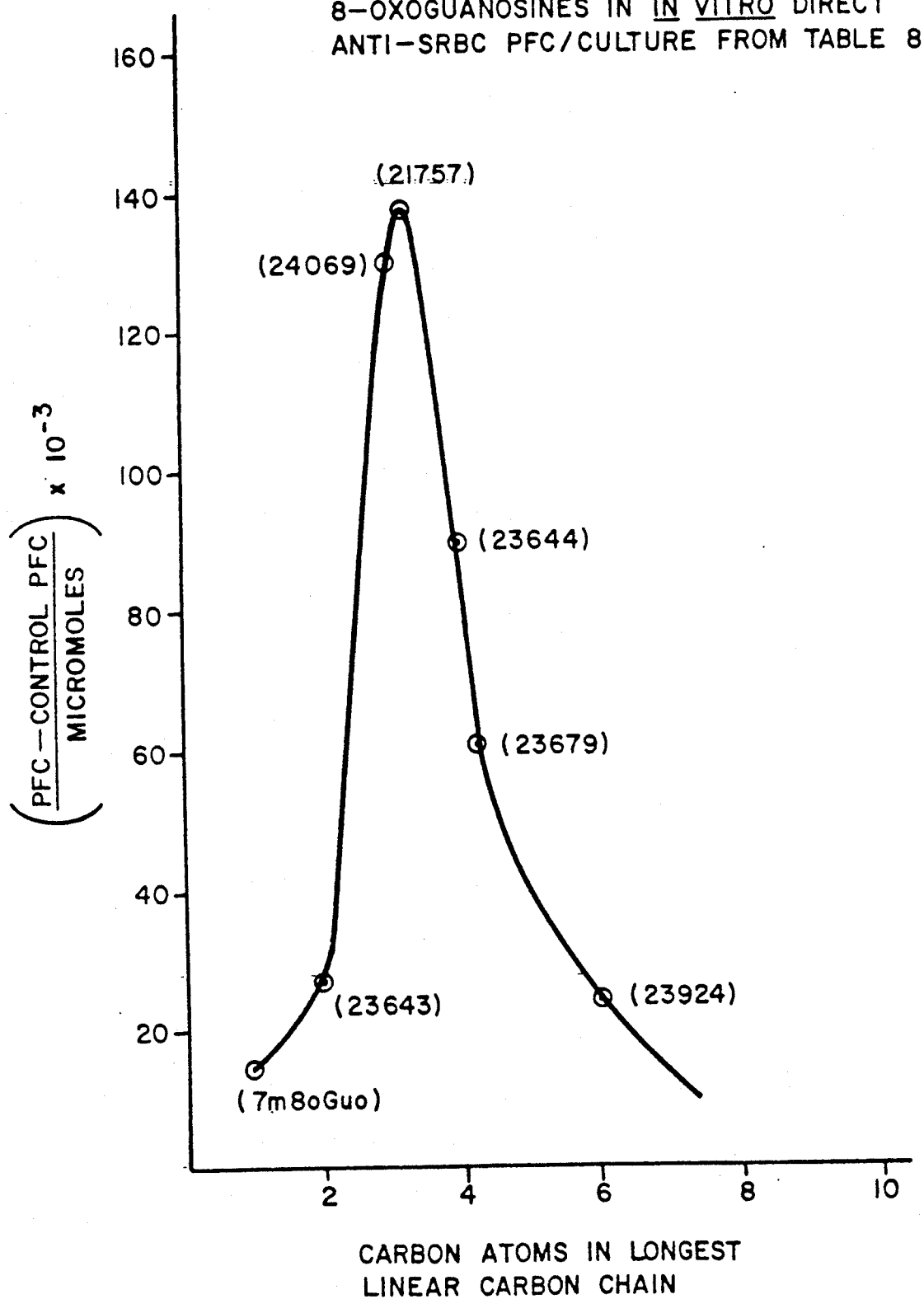

FIG. 5 is a graph showing the structure function relation between the length of a 7-substituent of a 7-hydrocarbyl-substituted-8-oxoguanosine and the antigen-specific PFC response of murine lymphocytes to SRBC in vitro. PFC values are from Table 8 at $1 \times 10^{-5}$ molar (M) guanosine derivative. Data points are for 7m8oGuo, the 7-ethyl (23643), 7-allyl (21757), 7-propyl (24069), 7-butyl (23644), 7-(2-butenyl) (23679) and 7-hexyl (23924) derivatives. Each value for direct anti-SRBC PFC/culture less the control value was divided by the micromoles of guanosine derivative present in the 1 ml cultures [$(1 \times 10^{-5}$ M$)/(10^{-3}$ liters$)$] to obtain the ordinate values. The abscissa coordinates correspond to the number of carbon atoms present in the longest linear carbon atom chain of the 7-substituent. The allyl chain was taken to be slightly longer than propyl, and 2-butenyl was taken to be slightly longer than butyl. Further details regarding this graph are provided hereinafter.

Figure 6:
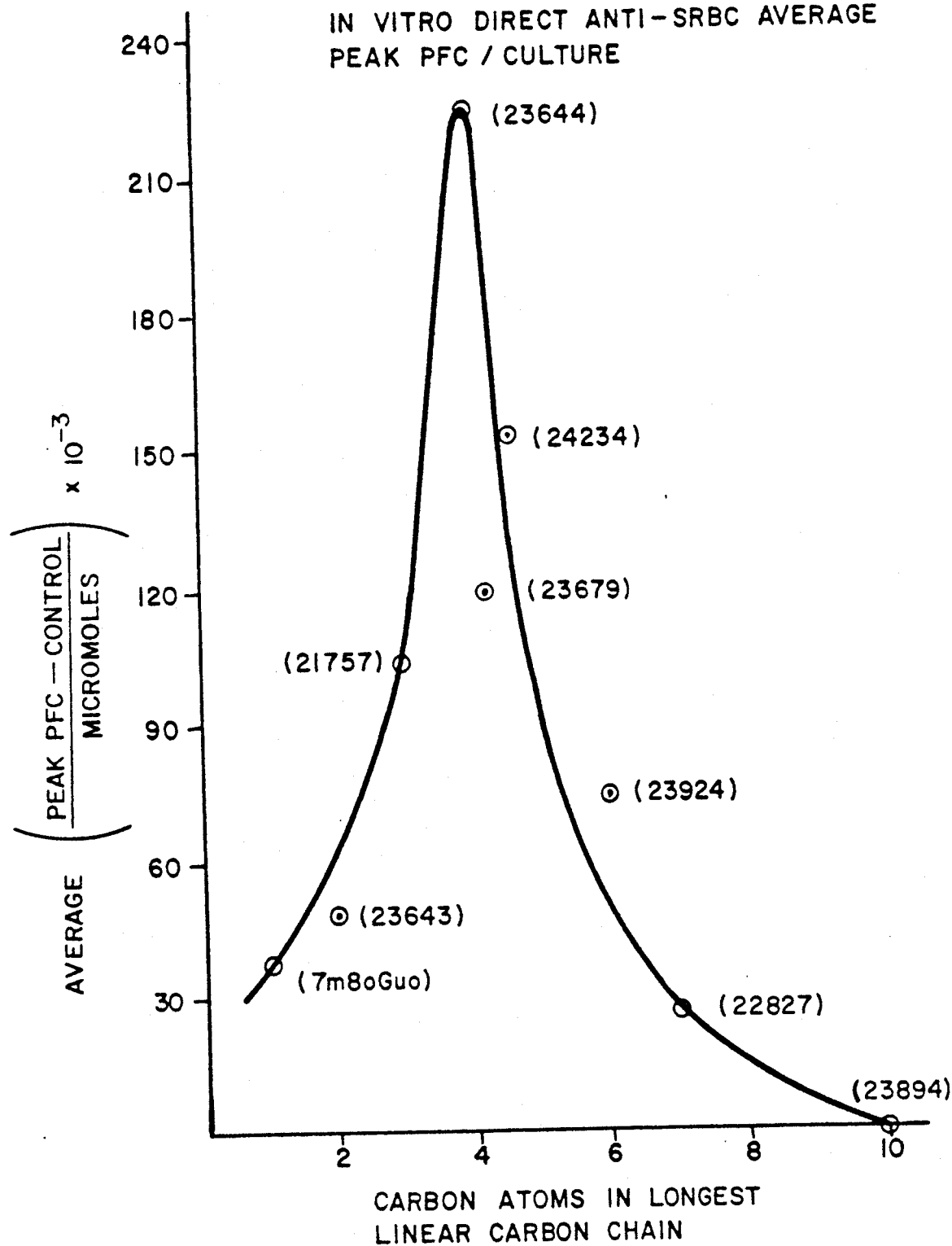

FIG. 6 is another graph similar to the graph of FIG. 5. The data points for this graph were obtained over a period of time from several studies using murine lymphocytes from several animals. Average peak direct anti-SRBC PFC-control PFC values are plotted versus the number of carbon atoms present in the longest linear carbon atom chain of the 7-substituent. Peak values were obtained by first subtracting the control PFC/culture from each data point obtained at differing guanosine derivative concentrations to obtain a "net" PFC value. Each net PFC value so obtained was thereafter divided by the micromoles of guanosine present in the study that produced that net value to obtain a peak PFC value per micromole. Peak PFC per micromole values so obtained for each guanosine derivative from studies utilizing the particular derivative were thereafter averaged. Those average values are shown on the graph.

Parenthesized five digit numbers used herein to identify guanosine derivatives are also used in this Figure, and are the same as those of FIG. 5. In addition, data for the 7-benzyl (24234), 7-cinnamyl (22827) and 7-decyl (23894) 8-oxoguanosines are also shown in FIG. 6.

Abscissa coordinates for guanosine derivatives that also appear in FIG. 5 are repeated in this Figure. In addition, the 7-benzyl derivative was assigned an abscissa coordinate of slightly less than pentyl, and the 7-cinnamyl derivative was assigned an abscissa coordinate of slightly less than heptyl. Further details concerning this Figure are provided hereinafter.

The present invention has several benefits and advantages.

One salient benefit of the present invention is that its compounds are generally more effective; i.e., provide a similar response at a lower dose or provide an enhanced response at a given dose, than previously known guanosine immunostimulants.

An advantage of the invention is that use of one of its compositions can provide the second message required for B lymphocyte activation and differentiation in response to a first (antigenic) message.

Another benefit of the invention is that an enhanced immune response can be effected in both the presence and absence of T helper cell activity. Thus, an enhanced immune response is noted in both T cell-dependent and T cell-independent systems.

Another advantage of this invention is that particular immune-suppressed and immune-deficient conditions and disease manifestations can be improved and lessened by use of the invention.

Still further benefits and advantages of the invention will be apparent to those skilled in the art from the discussion that follows.

Anthropomorphic descriptions such as the sending and receiving of messages by and to chemicals and cells are used herein for descriptive purposes as aids to the understanding of observed phenomena.

DETAILED DESCRIPTION OF THE INVENTION

I. Introduction

The present invention contemplates an immune response-enhancing agent (immunostimulator) that stimulates the immune system of the host mammal to which it is administered as well as stimulating leukocytes in cell culture. The immunostimulation particularly contemplated is predominantly antigen-specific for the immunizing antigen.

In studying the effects of some reportedly mitogenic guanosine derivatives, e.g., guanosine 3',5'-cyclic monophosphate and its 8-bromo derivative, it was found that a new class of low molecular weight guanine nucleoside derivatives, when present in an effective amount as the active ingredient of a composition containing a diluent amount of a physiologically tolerable carrier, provided remarkable effects in modulating responses of mammalian cells. Enhancement of antigen-specific humoral immune responses, which resulted in potent adjuvanticity, T cell replacing factor-like activity, T helper activity, T cell-derived lymphokine secretion, cytotoxic T cell activity and immunoreconstitution activity are particular examples of the cellular responses that were found to be modulated. Those compounds and their methods of use are disclosed in U.S. Pat. Nos. 4,539,205 and 4,643,992.

The compounds of the present invention have been found to be surprisingly more active than were the compounds of the above two patents. The findings of enhanced activity were surprising for a number of reasons.

The most active compound disclosed in the above U.S. patents was 7-methyl-8-oxoguanosine (7m8oGuo), both as a leukocyte mitogen and an antigen-specific adjuvant. As will be discussed hereinbelow, mitogenicity and adjuvanticity are phenomena that are not of necessity related.

In view of subsequently obtained data, it was surprising that 7m8oGuo exhibited enhanced activity over compounds such as 8-hydroxyguanosine (referred to as its tautomer, 8-oxoguanosine; 8oGuo), or 8-mercaptoguanosine (referred to as 8MGuo, or as its tautomer 8-thioxoguanosine). More specifically, subsequent data, some of which are provided hereinafter as exemplary, revealed that the activity (both mitogenicity and adjuvanticity) of a series of 8-substituted guanosines decreased with increasing size of the 8-substituent group.

Thus, since the methyl group of 7m8oGuo is bonded on the guanosine ring adjacent to the 8-position where a substituent size effect was found, the addition of that group or any group at the 7-position where there previously was no substituent would have been expected to also cause a decrease in activity merely because the molecule in question was larger at a position adjacent to the size-sensitive ring position. The enhanced adjuvanticity of compounds of the present invention having still larger substituents at the 7-position on the guanosine ring over 7m8oGuo was still more unexpected and surprising.

II. The Compounds

The immunostimulating compounds contemplated herein are 7,8-disubstituted guanine nucleoside derivatives (also referred to herein as guanosines or guanosine derivatives). These compounds have structures that correspond to formula I shown below:

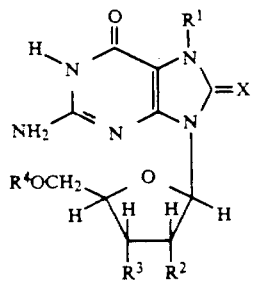

wherein X is O, S, Se or NCN;

$R^1$ is a straight, cyclic or branch chain hydrocarbyl radical having a length greater than an ethyl group and less than a decyl group;

$R^2$ and $R^3$ are the same or different radicals selected from the group consisting of hydrogen, hydroxyl, lower alkoxy, lower alkanoyloxy and benzoxy radicals or $R^2$ and $R^3$ together constitute lower alkylidenedioxy radical;

$R^4$ is a radical selected from the group consisting of hydrogen, lower alkanoyl and benzoyl.

It is noted that the ribosyl group in the formula above is intended to be shown bonded at the 1-position of that ring with the bond being in the beta-configuration. In addition, the D form of the ribosyl group is to be understood as intended.

Preferred guanosine derivatives are those in which X is O or S, $R^1$ has a length greater than ethyl and less than hexyl, and $R^2$ and $R^3$ are hydroxy or acetoxy. In particularly preferred practice, X is O, $R^1$ is selected from the group consisting of propyl, allyl, butyl, 2-butenyl, and benzyl, $R^2$ and $R^3$ are hydroxyl, and $R^4$ is hydrogen. Most preferably, X is O, $R^1$ is allyl, $R^2$ and $R^3$ are hydroxyl and $R^4$ is hydrogen.

As noted previously, an $R^1$ radical has a length greater than that of an ethyl group. An $R_1$ radical also has a length that is less than that of a decyl group. That is to say that $R^1$ is a hydrocarbyl radical having a length greater than that of a saturated two carbon chain, and shorter than that of a saturated ten carbon chain; each length including appropriate hydrogen atoms. A hydrocarbyl group referred to simply as propyl, butyl, hexyl, decyl or the like is to be understood to be a normal, straight chain radical. Branch chain radicals are indicated by usually used numerical or abbreviated prefixes such as 2-propyl or iso-propyl, respectively.

The hydrocarbyl radical chain lengths are measured along the longest linear carbon chain in the molecule. Such lengths can be readily determined by using published bond angles, bond lengths and atomic radii, as needed, to draw and measure a staggered chain, or by building models using commercially available kits whose bond angles, lengths and atomic radii are in accord with accepted, published values. Radical lengths can also be determined somewhat less exactly by assuming unsaturated bonds to have the same length as saturated bonds and that bond angles for unsaturated bonds are the same as those for saturated bonds, although the above-mentioned modes of measurement are preferred. The lengths are determined as the longest length for the radical.

$R^1$ is a hydrocarbyl radical having a particular length. Being a hydrocarbyl radical, $R^1$ groups contain only carbon and hydrogen atoms.

Hydrocarbons and hydrocarbyl radicals can broadly be divided into aliphtic and aromatic radicals. Aliphatic radicals include (i) saturated alkane (alkyl radicals) and (ii) mono- and poly-unsaturated alkenes and alkynes (alkenyl and alkynyl radicals), respectively. Cyclic, straight chain and branch chain radicals exist for each type of aliphatic radical. Aromatic $R^1$ radicals include an aromatic benzene or a naphthalene ring. Aralkane, aralkene and aralkyne radicals that contain an aromatic ring linked to an aliphatic group are also contemplated, as are alkyl substituted benzene and naphthalene derivatives. Exemplary $R^1$ radicals are described below.

As already noted, $R^1$ radicals have a length greater than that of an ethyl group and a length shorter than that of a decyl group. Alkyl radicals of that group can therefore be referred to as $C_3-C_9$ alkyl radicals. The $C_3-C_9$ alkyl radicals include several members of the class referred to herein as "lower alkyl" radicals that are also useful as portions of $R^2$, $R^3$ and $R^4$ radicals as is discussed hereinafter. Thus, it is appropriate at this place to discuss lower alkyl radicals.

Groups and radicals referred to herein as "lower" denote that they contain 1 to about 6 carbon atoms. This definition applies to the use of the word "lower" as it is used in all of $R^1$, $R^2$, $R^3$ and $R^4$. For $R^2$, $R^3$ and $R^4$, it is preferred to use a "lower" radical that contains 1-3 carbon atoms.

Lower alkyl radicals include both straight chain and branch chain groups such as, for example, methyl, ethyl, propyl, iso-propyl, n-butyl, sec-butyl, t-butyl, n-pentyl, 3-methyl-2-butyl, 1-methylbutyl, 2-methylbutyl, neo-pentyl, n-hexyl, 1-methylpentyl, 3-methylpentyl, 1-ethylbutyl, 2-ethylbutyl, 2-hexyl, 3-hexyl, and the like. The group of $C_3-C_9$ alkyl radicals of $R^1$ excludes methyl and ethyl radicals of the group of lower alkyl radicals, and includes heptyl, octyl and nonyl radicals as well as further branch chain radicals such as the 2-methylheptyl radical that are alkyl substituted alkyl radicals. More preferred $R^1$ radicals have a length greater than ethyl and less than hexyl and have a straight chain; more preferred lower alkyl radicals for $R^1$ include propyl, butyl, and pentyl.

Cyclic aliphatic radicals are also contemplated, and can be included in the group of alkyl radicals as well as in the group of unsaturated alkenyl and alkynyl radicals. Such radicals include cyclopentyl, cyclohexyl, cycloheptyl and cyclooctyl radicals. Also included in this group are unsaturated radicals such as 2-cyclopentenyl, 2-cyclohexenyl, 3-cycloheptenyl and the like.

Contemplated cyclic aliphatic radicals further include radicals having one or more lower alkyl substituents bonded to a ring, where the ring is bonded directly to the 7-position of a guanine ring, as well as those radicals having an alkylene, alkenylene or alkynylene radical bonded between the 7-position nitrogen atom and the cyclic ring structure. Exemplary radicals of the former group of cyclic radicals include 2-methylcyclopentyl, 3-ethylcyclohexyl and 4-iso-propylcycloheptyl. Exemplary radicals of the latter group of cyclic radicals include 2-(cyclopentyl)ethyl, 3-(cyclohexyl)butyl and the like.

Unsaturated radicals constitute yet another group of aliphatic radicals. Exemplary monounsaturated compounds include 3-butenyl, 2-methyl-3-pentenyl, 3-hexynyl and the like. Cyclic radicals that also contain one or more unsaturated bonds but are aromatic are considered as cyclic radicals, as above. Polyunsaturated radicals include butadienyl, 2-methyl-2,4-pentedienyl and the like.

$C_3-C_6$ Beta-alkenyl radicals are a particularly preferred group of unsaturated hydrocarbyl radicals. $C_3-C_6$ Beta-alkenyl radicals contain an ethylenic double bond beta to the 7-nitrogen atom of the guanosine. Exemplary radicals include allyl (2-propenyl), 2-butenyl, 2-pentenyl, 3-methyl-2-pentenyl and the like.

Aromatic radicals constitute another group of hydrocarbyl, $R^1$, radicals Exemplary aromatic radicals include phenyl and naphthyl radicals. Alkyl-substituted aromatic radicals such as 3- or 4-methylphenyl, 3- or 4-isopropylphenyl, 3-ethylnaphthyl, 5-methylnaphthyl radicals and the like are also contemplated.

Aralkyl radicals are further contemplated $R^1$ radicals. Benzyl, phenethyl and 3-phenylbutyl radicals are exemplary of this group. Benzyl is a particularly preferred $R^1$ radical.

The cinnamyl radical (3-phenyl-2-propenyl) is a closely related radical, being an aralkenyl radical. The cinnamyl radical can also be viewed as a substituted beta-alkenyl radical that is longer than a $C_3-C_6$ beta-alkenyl radical, but is surprisingly active as an adjuvant for its length.

$R^2$ and $R^3$ radicals can be the same or different, and are selected from the group consisting of hydrogen, hydroxyl, lower alkoxy, lower alkanoyloxy and benzoxy. $R^2$ and $R^3$ together can also form a 2',3'-cyclic lower alkylidenedioxy radical. Exemplary $R^2$ and $R^3$ radicals are discussed below.

Lower alkoxy radicals are lower alkyl radicals bonded to the guanine sugar ring through an oxygen atom. Exemplary lower alkoxy radicals include methoxy, ethoxy, iso-propoxy, butoxy, hexyloxy and the like. Lower alkanoyloxy radicals are esters formed between a guanine sugar ring hydroxyl group and a lower alkyl carboxylic acid. Examples of lower alkanoyloxy radicals include formoxy, acetoxy, propionoxy, hexanoyloxy and the like.

Lower alkyl acetal and ketal derivatives of the 2'-, and 3'- hydroxyl groups are referred to as 2',3'-cyclic lower alkylidenedioxy or more simply as lower alkylidenedioxy radicals. These radicals are formed by reaction of an aldehyde such as formaldehyde, acetaldehyde or the like, or a ketone such as acetone or methylethyl ketone with the 2'- and 3'-hydroxyl groups of a substituted guanosine ribosyl group.

It is preferred that $R^2$ and $R^3$ be hydroxyl, lower alkanoyloxy or benzoxy, and more preferably hydroxyl or acetoxy. When $R^2$ and $R^3$ are lower alkanoyloxy or benzoxy, those radicals may be lost during or soon after the leukocyte contacting step of a method of the invention, and thus may provide a "pro drug" form of the guanosine derivative. Most preferably, $R^2$ and $R^3$ are hydroxyl.

$R^4$ is a radical selected from the group consisting of hydrogen, lower alkanoyl and benzoyl. $R^4$ is most preferably hydrogen. When $R^4$ is lower alkanoyl or benzoyl, it is also believed that the carboxyl group may be cleaved as described above, again providing a "pro drug".

A useful guanosine is substantially free from ionic charge at physiological pH values; i.e., about pH 7.0 to about pH 7.5, except for the ionic charges that might be provided by the relatively acidic 1-position ring nitrogen atoms. Thus, a useful molecule is free of acid and base-containing moieties that are not present in guanosine. That freedom from acidic and basic groups extends from the $R^1$ radical, by definition, and throughout the whole guanosine molecule.

The guanines are acids, and as such can form base addition salts. Such salts are useful in providing storage stability and do not provide an added ionic charge to a guanine derivative used in a method of the invention because of the buffering effect provided by the host's blood and lymph systems or the buffer of a culture medium.

Pharmaceutically acceptable, non-toxic base addition salts of guanine derivatives are useful herein, and can be formed by treatment of the immune response-enhancing agent with an appropriate base, in a suitable solvent such as water or a lower alkyl alcohol such as methanol or ethanol. Exemplary inorganic bases include sodium, potassium and ammonium hydroxide, and the like bases. Exemplary organic bases include tris-(hydroxymethyl)-aminomethane (TRIS), 4-(2-hydroxyethyl)-1-piperazine-ethanesulfonic acid (HEPES) and the like bases. Conversely, the base addition salt form can be converted to the free guanosine form by treatment with acid.

The substituted guanine nucleoside derivatives useful herein are readily prepared by procedures published in the chemical literature, or by procedures analogous thereto. Several exemplary syntheses are provided hereinafter in the Materials and Methods Section. Syntheses of 7,8-di-substituted guanine nucleoside derivatives typically begin with the 9-1'-beta-aldoglycoside bond already formed, although the initial formation of that bond is not required. A novel and unexpected method of synthesizing some of the compounds of this invention is discussed hereinafter in Section V.

In addition to the exemplary syntheses described hereinafter, three general synthetic modes are described briefly here. These modes are exemplary of the synthetic modes provided by the literature, and are described using a 7-hydrocarbyl-substituted-8-thioxoguanosine of the invention as the compound to be prepared.

In a first mode, a 7-hydrocarbyl-substituted-8-thioxoguanine is reacted with a suitable alpha-1-leaving group-substituted ribose derivative such as alpha-1-chloro (or bromo or acetoxy)-2,3,5-tribenzyoyl-D-ribose in a suitable solvent to form the beta-ribosyl derivative. The reaction products are collected, separated by HPLC to obtain the desired guanosine derivative.

In a second mode, 7-allyl-8-thioxoguanosine (22444; Example 9) is oxidized to form the corresponding aldehyde. The resulting 7-(2-ethanal)-8-thioxoguanosine is thereafter condensed via a Wittig reaction to form a 7-beta-$C_3$-$C_6$ alkenyl (or other) radical-substituted guanosine that is separated from other products present for use. That unsaturated guanosine can thereafter be reduced to form a saturated substituent.

In a third mode, ring closure by a reaction of thiophosgene with an appropriately substituted 2,5,6-triamino-4-hydroxypyridmidine is utilized. More specifically, a 2-amino-4-hydroxy-5-hydrocarbyl-substituted-amino-6-beta-D-ribosylpyrimidine is reacted with thiophosgene in the presence of an acid-scavenging base to provide a 7-hydrocarbyl-8-thioxoguanosine derivative that can be separated from other reaction products for use.

III. The Compositions

A composition of this invention comprises a diluent amount of a physiologically tolerable carrier admixed with an immunopotentiating (immune response-enhancing or immunostimulating) effective amount of an substituted guanine nucleoside derivative of this invention described before.

A composition for in vivo administration is provided for per oral or parenteral administration in customary unit dosage compositions. The term "unit dosage" and its grammatical equivalents as used herein refer to physically discrete units suitable as unitary dosages for human patients and other mammals, each unit containing a predetermined effective amount of the guanosine active ingredient calculated to produce the desired therapeutic effect in association with the required physiologically tolerable carrier, e.g. a diluent or a vehicle. The specifications for the novel unit dosage forms of this invention are dictated by and are directly dependent on (a) the unique characteristics of the active guanosine derivative ingredient and the particular therapeutic effect to be achieved, and (b) the limitations inherent in the art of compounding such an active ingredient for therapeutic use in vitro, as well as in vivo in humans and other animals.

Examples of suitable unit dosage forms in accord with this invention are tablets, capsules, pills, powder packets, granules, wafers, and the like, segregated multiples of any of the foregoing, as well as liquid solutions, emulsions and suspensions. Liquid compositions can be administered in usual manners such as subcutaneously, intraperitoneally, intramuscularly, perorally or the like.

The amount of active ingredient that is administered in vivo as an effective immunostimulating amount depends on the age and weight of the patient, the particular condition to be treated, the frequency of administration, and the route of administration. The total daily dose range can be about 0.01 to about 200 milligrams per kilogram of body weight, more preferably about 0.1 to about 25 milligrams per kilogram of body weight, and most preferably about 1 to about 15 milligrams per kilogram of body weight. The human adult dose is in the range of about 5 to about 1400 milligrams daily, given either as a single dose or in 3 or 4 divided doses. Veterinary dosages correspond to human dosages with the amounts administered being in proportion to the weight and metabolic rate of the animal as compared to adult humans.

It will be appreciated by those skilled in the art that useful in vivo concentrations can vary from animal species to animal species. Those skilled workers also know that appropriate concentrations can be readily determined.

Concentrations for the in vitro contacting of animal cells are about $1 \times 10^{-6}$ molar to about $3 \times 10^{-4}$ molar for cell concentrations of about $10^6$–$10^7$ cells per milliliter. More preferably, the concentration is about $1 \times 10^{-5}$ molar to about $1 \times 10^{-4}$ molar. As will be seen from the Results Section hereinafter, the peak concentration; i.e., the concentration that provides the greatest adjuvanticity, for a given guanosine can vary as much as 10–100 fold when studied in mouse or human lymphocyte systems.

A composition can be a solid or a liquid. Physiologically tolerable carriers are well known in the art. Exemplary of liquid carriers are sterile aqueous solutions that contain no materials in addition to the active ingredient guanosine derivative and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes The latter carriers are exemplified by Ringer's Injection, Dextrose Injection, Dextrose and Sodium Chloride Injection and Lactated Ringer's Injection.

Liquid compositions can also contain liquid phases in addition to and to the exclusion of water. Exemplary of such additional phases are glycerin, vegetable oils, such as cotton seed oil, sesame oil and water-oil emulsions.

Exemplary solid carriers include those materials usually used in the manufacture of pills or tablets, and include corn starch, lactose, dicalcium phosphate, thickeners such as tragacanth gum and methylcellulose U.S.P., finely divided $SiO_2$ polyvinylpyrrolidone, magnesium stearate and the like. Additionally, the solid carrier can include biodegradable and non-biodegradable polymers, polypeptide carriers, affinity carriers such as AFFI-GEL 601 (phenyl boronate resin available from BIO-RAD Laboratories, Richmond, Calif.), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide aspartic-phenylalanine methyl ester sweetener sold under the tradename NUTRASWEET (aspartame) by G. D. Searle Co.

IV. Method of Immunostimulation

A method of enhancing the immune response of leukocytes is also contemplated. Preferably, the immune response is an antigen-specific response. In accordance with this method, leukocytes such as B cells, T cells, neutrophils and macrophages are contacted separately or in combination in an aqueous medium with a before-described composition containing an immunostimulating effective amount of a before-described guanine nucleoside derivative.

The method can be practiced in vivo in humans, laboratory mammals such as mice, rats and guinea pigs or in veterinary animals and pets such as pigs, horses, cattle, dogs and cats. The method can also be practiced in vitro in cell cultures such as in hybridoma culture for the production of monoclonal antibodies.

The leukocytes are contacted in an aqueous medium regardless of whether the composition of guanosine derivative is itself a solid or liquid, or whether or not the liquid of the composition is aqueous. For the in vivo method, the aqueous medium is supplied at least in part by the water of the blood or lymph. For in vitro methods, the aqueous medium is supplied at least in part by the culture medium used.

Contact between the composition and leukocytes is maintained for a time period sufficient for the contacted cells to manifest the enhancement of their immune response. That immunostimulation can itself be manifest in cellular proliferation, enhanced antibody secretion, enhanced T helper activity, enhanced cytokine production from T cells and macrophages, enzyme secretion from neutrophils, and the like. The results discussed hereinafter illustrate a non-specific mitogenic responses of murine spleen cells, antigen-specific responses of murine B cells and human peripheral blood lymphocytes depleted of T suppressor cells, antigen-specific proliferation of T cells, the in vitro reconstitution of the primary immune response in murine immunodeficient B cells, T suppressor cell-replacing activity for an antigen-specific response in murine B cells, and an in vivo antigen-specific enhancement of murine antibody production. These enhanced immune responses are to be taken as illustrative of the use of a method of the invention and are not intended to be limiting.

For use in vivo, contact between leukocytes and optimal concentrations of the composition is typically maintained for a time period sufficient for the animal to clear the guanosine derivative from its body as by metabolism, excretion or both processes. That time period can be longer than that required for immunostimulation to be manifest. Contact with an individual unit dose is typically maintained for a time period of hours to about a week or more, depending upon the carrier or vehicle used. Continual contact can be advantageous for an immunodeficient animal host.

Contact in vitro can be maintained for a period of time sufficient for one of the before-described immunostimulations to become manifest as determined by standard assay techniques. Such maintenance times typically take about one to about seven days of time, and more usually about 2 to about 6 days.

V. Synthesis Method

The present invention further contemplates a method of synthesizing 7-allyl or 2-hydrocarbyl-substituted-allyl 8-oxo,-8-thioxo or 8-selenoxo purine derivatives whose 9-position nitrogen atom is blocked from reacting. The purine derivatives particularly contemplated are derivatives of guanosine, adenosine, and inosine or their deoxyriboside analogs. The purine most preferably formed is a guanosine derivative as is herein discussed in detail.

The 9-position nitrogen atoms for the particularly contemplated purines are blocked from reacting by being bonded to a blocking group. Most preferably, the blocking group is a ribosyl or deoxyribosyl radical, and the guanine is bonded 9,1'-beta to the ribosyl or deoxyribosyl radical. Other blocking groups including other 1-glycosides such as glucosyl and arabinosyl, acyl groups such as acetyl, benzoyl and t-butyloxycarbonyl and other removable and non-removable blocking groups such as benzyl and $C_2$–$C_6$ alkyl, respectively, are contemplated. The specific identity of the 9-position blocking group is not believed to be of import so long as that group does not interfere with the reaction at the 8- and 7-positions of the purine molecule. Similarly, other substituents can be present at the 1-, 2- and 6-positions of the purine so long as they do not interfere with the reaction.

In accordance with this method, a purine starting material is provided substituted at its 8-position by a group —X—CH$_2$CR=CH$_2$, wherein X is O, S or Se, and R is hydrogen, lower alkyl or benzyl. The 8-substituted purine starting material is heated to an elevated temperature of about 50° C. to about 200° C. The elevated temperature is maintained for a time sufficient (about one hour to about two weeks) for the 8-substituted starting material to rearrange and form a purine product substituted (i) at the 8-position by the group =X, wherein X in the product is the same as that X in the starting material, and (ii) at the 7-position by a group —CH$_2$—CR=CH$_2$, wherein R is the same as that of the starting material. The product 7,8-disubstituted-9-blocked purine derivative is preferably isolated as can be accomplished by well known means.

The above reaction is preferably carried out with the purine starting material dissolved or dispersed in a liquid solvent medium that is inert to the reaction conditions. Exemplary inert liquid solvents for such purposes include water, dimethyl formamide and dimethyl sulfoxide as are described hereinafter in the Materials and Methods Section.

It is noted that the starting purine derivative need not be an isolated, purified material. Rather its presence can be circumstantially inferred from the structure of precursor reactants and the final product as by carrying a crude reaction mixture provided by the formation of the 8-oxo-, 8-thioxo- or 8-selenoxoallyl compound through the rearrangement step.

The temperatures useful in the above reaction and the duration of their maintenance can vary widely. Optimal temperatures appear to be about 100° C. where X=O and about 135° where X=S or X=Se. The sulfur analog required a longer reaction time than did either the oxygen or selenium analogs.

Without wishing to be bound by theory, it is believed that the described reaction is a rearrangement that proceeds via a six-membered ring intermediate or transition state. That six-membered ring is thought formed by the 7-nitrogen and 8-carbon atoms of the purine ring, the X atom and the first three (delineated) carbon atoms of the X—CH$_2$—CR=CH$_2$ group, with the =CH$_2$ carbon atom of the starting material closing the ring by forming a bond with the 7-nitrogen atom.

In another aspect of this embodiment of the invention, the rearrangement is catalyzed using palladium dichloride (PdCl$_2$) in a relatively low boiling solvent such as tetrahydrofuran boiling point =65° C.). As in the case for the uncatalyzed rearrangement, the various reactive moieties on the guanosine, in addition to the 9-position nitrogen atom, such as each of the sugar ring hydroxyl groups, the 6-oxo (hydroxy) group and the 2-amino group are typically blocked during the catalyzed rearrangement with suitable removable blocking groups such as trimethylsilyl groups. Such blocking is not required for the uncatalyzed reaction.

In an exemplary catalyzed rearrangement the 9-blocked—8—X—CH$_2$—CR=CH$_2$ guanosine derivative starting material is admixed with a catalytic amount of PdCl$_2$, at a catalyst to guanosine mole ratio of about 1:1 to about 1:10, and the resulting admixture is refluxed in a solvent such as tetrahydrofuran for a suitable time period, such as about 10 to about 20 hours to effect the rearrangement. The products of the reaction are thereafter typically separated and collected.

Where removable blocking groups are employed during the synthesis, those blocking groups are also typically removed prior to collecting the desired 7—CH$_2$—CR=CH$_2$—8—X—guanosine derivative product. Where trimethylsilyl groups are used as removable blocking groups, those groups can be removed by treatment of the blocked product with an acid such as acetic acid.

As will be seen from an examination of Example 9 hereinafter, the catalyzed reaction provided a higher yield of 7a8MGuo (42.5 percent) than did the uncatalyzed reaction (36 percent), and did so in a shorter reaction time; i.e., 16 hours vs. 9 days, and at a lower temperature; i.e., 65° vs. 130° C. For the catalyzed reaction, the rearrangement is typically carried out at a temperature of about 50° to about 100° C., whereas the uncatalyzed rearrangement is typically carried out at a temperature of about 100° to about 200° C.

VI. Results

Specific results utilizing the compounds, compositions and methods of this invention have been obtained, and those results have often been compared to similar results obtained using compounds, compositions and methods disclosed in U.S. Pat. No. 4,643,992. The majority of these results have been obtained using 7-(2-propenyl)-8-oxoguanosine [also referred to herein as 7-allyl-8-oxoguanosine) and 7-(2-propenyl)-8-thioxoguanosine [also referred to herein as 7-allyl-8-thioxoguanosine and 7-allyl-8-mercaptoguanosine]. Those two compounds are conveniently referred to as 7a8oGuo and 7a8MGuo, respectively, using the same shorthand notation discussed previously for 7-methyl-8-oxoguanosine (7m8oGuo), 8-mercaptoguanosine (8MGuo) and 8-oxoguanosine (8oGuo). Another shorthand notation used for a compound in comparisons is 8-BrGuo for 8-bromoguanosine.

The results discussed hereinafter were obtained using one or more compounds of the invention, unless otherwise noted, in a composition of the invention that is used in a method of the invention. For brevity, and ease of description, only the compounds will be referred to hereinafter with the understanding that such compounds are utilized in compositions and methods of the invention.

Each of the new compounds whose activity is discussed or compared herein has also been given an identifying five-digit number. Those numbers are listed in the title of the Example that describes preparation of the compound. The five-digit number and/or the Example number is utilized in the tables and discussion that follow to assist in identifying those compounds.

A. Activities of 8-Substituted Guanosines

As noted earlier, the adjuvanticity and mitogenicity of a series of 8-substituted guanosines not of this invention having thioethers of varying lengths were examined. The results of those studies are shown in Tables 1 and 2 below in which horizontal lines across the whole table are used to distinguish separate studies from each other.

TABLE 1

Antigen-Specific Adjuvanticity of 8-Thioether guanosines[1]

| Compound[2] | Concentration[3] | Direct Anti-SRBC PFC/Culture[4] | |
|---|---|---|---|
| | | CBA/CaJ | C57BL/6J |
| 22359 | $10^{-4}$ | 123 ± 21 | — |
| (cinnamyl;11) | $3 \times 10^{-4}$ | 157 ± 7 | 2620 ± 100 |
| | $10^{-3}$ | 653 ± 52 | 3110 ± 350 |
| 22435 | $10^{-4}$ | 247 ± 38 | — |
| (2-butenyl;3) | $3 \times 10^{-4}$ | 582 ± 52 | 9130 ± 1110 |
| | $10^{-3}$ | 607 ± 57 | 12,080 ± 470 |
| 8MGuo | $3 \times 10^{-4}$ | 527 ± 25 | 11,000 ± 140 |
| Control | (No nucleoside) (Antigen present) | 75 ± 10 | 486 ± 70 |
| 22300 | $10^{-4}$ | 420 ± 105 | — |
| (allyl;9) | $3 \times 10^{-4}$ | 870 ± 70 | — |
| | $10^{-3}$ | 490 ± 133 | — |
| 8MGuo | $10^{-4}$ | 813 ± 129 | — |
| | $3 \times 10^{-4}$ | 782 ± 123 | — |
| Control | (No nucleoside) (No antigen) | 8 ± 4 | — |
| Control | (No nucleoside) (Antigen present) | 307 ± 61 | — |

[1] Adjuvanticities against sheep red blood cells [SRBC] measured in direct plaque-forming cells per culture of lymphocytes from the mouse strains shown. Details of the procedure are provided in the Materials and Methods Section. Standard errors from the enumerated mean values are shown by "± number".
[2] The nucleosides are identified by their five digit numbers. The radical bonded to the 8-thio group and the Example number in which the compound's preparation is shown is within the parenthesis.
[3] Concentration of the nucleoside in moles per liter in the aqueous medium in which the lymphocytes were contacted.
[4] Lymphocytes from inbred mouse lines CBA/CaJ or C57BL/6J were used.

TABLE 2

Mitogenicity of 8-Thioetherguanosines[1]

| Compound[2] | Concentration[3] | [$^3$H] TdR Uptake (cpm/culture) |
|---|---|---|
| 22359 | $10^{-4}$ | 1600 ± 90 |
| (cinnamyl;11) | $3 \times 10^{-4}$ | 1300 ± 80 |
| | $10^{-3}$ | 1700 ± 280 |
| 22435 | $10^{-4}$ | 4500 ± 120 |
| (2-vutenyl;3) | $3 \times 10^{-4}$ | 8800 ± 200 |
| | $10^{-3}$ | 11,200 ± 202 |
| 8MGuo | $10^{-3}$ | 41,100 ± 390 |
| Control | (No nucleoside) | 2100 ± 60 |
| 22300 | $10^{-4}$ | 2700 ± 130 |
| (allyl;9) | $3 \times 10^{-4}$ | 4100 ± 70 |
| | $10^{-3}$ | 16,400 ± 1130 |
| 8MGuo | $10^{-3}$ | 25200 ± 950 |
| Control | (No nucleoside) | 2400 ± 90 |

[1] Mitogenicity measured by the uptake of [$^3$H]TdR (tritium-labeled thymidine deoxyribonucleoside) as determined by measuring counts per minute (cpm) per cell culture using the conditions discussed in the Materials and Methods Section. Standard errors are shown as in Table 1.
[2,3] See notes 2 and 3 of Table 1.

The above results illustrate that as the length of the substituent increased, the activity of the 8-substituted guanosine derivative decreased relative to 8MGuo whole 8-sulfur atom was bonded only to a hydrogen atom. Thus, the antigen-specific adjuvanticity of the 8-(2-butenyl) derivative (22435) was greater than that of the longer 8-cinnamyl derivative (22359), but less than that of the 8-mercapto compound (8MGuo). The 8-allyl derivative (22300) had about equal adjuvanticity to that of 8MGuo for the concentrations shown. The results for mitogenicity for the same compounds showed an even more pronounced trend in activities with increasingly longer 8-substituents providing increasingly poorer results.

B. Adjuvanticity And Mitogenicity

The compounds, compositions and methods of the present invention are useful in inducing and enhancing mitogenic and polyclonal responses, and adjuvanticity as are the compounds whose activities are illustrated in Tables 1 and 2. The mitogenic and adjuvant properties of the present compounds are thought to result from at least two different pathways in which mitogenesis and a polyclonal response are often coincident results, whereas adjuvanticity results frequently differ. See, for example Goodman et al., *J. Exp. Med.*, 147:800 (1978) and McIntire et al., *J. Immunol.*, 117:674 (1976). Some similar differences are discussed in U.S. Pat. No. 4,643,992.

This uncoupling of activities is also shown for some of the compounds discussed herein as can be seen from the results of Tables 3 and 4, below.

TABLE 3

Antigen-Specific Adjuvanticity of Some 7-Substituted-8-oxoguanosines in the Human System[1]

| | | |
|---|---|---|
| 7m8oGuo | $10^{-4}$ | 2613 ± 192 |
| | $3 \times 10^{-4}$ | 5775 ± 214 |
| | $10^{-3}$ | 1517 ± 205 |
| 23643 | $10^{-4}$ | 5492 ± 137 |
| (ethyl;6) | $3 \times 10^{-4}$ | 9059 ± 310 |
| | $10^{-3}$ | 1950 ± 189 |
| 7a8oGuo | $10^{-4}$ | 10,075 ± 628 |
| | $3 \times 10^{-4}$ | 11,938 ± 762 |
| | $10^{-3}$ | 2,807 ± 381 |
| 23644 | $10^{-4}$ | 11,838 ± 1337 |
| (butyl;2) | $3 \times 10^{-4}$ | 12,238 ± 150 |
| | $10^{-3}$ | 7,363 ± 325 |
| Control | (No nucleoside) (No antigen) | 12 ± 4 |
| Control | (No nucleoside) (Antigen present) | 652 ± 86 |

[1] Studies were carried in a manner similar to those of Table 1, except that a human lymphocyte preparation was used.
[2,3] See notes 2 and 3 of Table 1.

TABLE 4

Mitogenicity of Some 7-Substituted-8-oxoguanosines in the Murine System[1]

| Compound[2] | Concentration[3] | [$^3$H] TdR Uptake (cpm/culture) |
|---|---|---|
| 7m8oGuo | $10^{-4}$ | 23,640 ± 770 |
| | $3 \times 10^{-4}$ | 39,620 ± 1160 |
| | $10^{-3}$ | 35,070 ± 1830 |
| 23643 | $10^{-4}$ | 37,490 ± 540 |
| (ethyl;6) | $3 \times 10^{-4}$ | 48,690 ± 1120 |
| | $10^{-3}$ | 34,160 ± 780 |
| 7a8oGuo | $10^{-4}$ | 39,830 ± 780 |
| | $3 \times 10^{-4}$ | 59,150 ± 420 |
| | $10^{-3}$ | 51,340 ± 1050 |
| 23644 | $10^{-4}$ | 30,720 ± 1030 |
| (butyl;2) | $3 \times 10^{-4}$ | 41,180 ± 410 |
| | $10^{-3}$ | 33,220 ± 1330 |
| Control | (No nucleoside) | 1640 ± 50 |

[1,2,3] See notes 1, 2 and 3 of Table 2.

The results shown in Table 4 illustrate that 7-methyl, 7-ethyl-, and 7-allyl- and 7-butyl-8-oxoguanosine all exhibited about the same mitogenicities in the murine system over the same concentration range. However, when adjuvanticity in the human system was examined (Table 3), peak values were about 100 percent greater for compounds of the present invention (7-allyl- and 7-butyl-8oxoguanosine) as compared to 7-methyl-8-oxoguanosine (7m8oGuo). Interestingly, human peripheral B cells, the same type of cells used in Table 3, that exhibit enhanced adjuvanticity in the presence of a guanosine derivative of this invention do not exhibit a mitogenic response in the presence of any guanosine derivative. The above results and the lack of mitogenicity exhibited by human cells that show an adjuvant response further confirm that mitogenicity and adjuvanticity are not necessarily linked and can proceed by different pathways.

C. Adjuvanticity Studies

A large number of comparisons of adjuvanticity using human and murine lymphocytes as the source of leukocytes have been carried out using compounds of the present invention, as well as with new compounds excluded from the present invention. Because of the differences in lymphocyte responses even from inbred mice, let alone the outbred human population, these results are best compared within a given study to those compounds used in the same study and to the controls for each study. Interstudy comparisons are however useful for showing trends and large differences. Tables 5, 6 and 7, hereinafter, provide exemplary data from such studies in which only the activity at the peak concentration is shown for each compound and the results for the controls are omitted. Results for each study are distinguished from the others by a horizontal line across the table.

TABLE 5

Adjuvanticity Studies in the Murine System[1]

| Compound[2] | Peak Concentration[3] | Peak Direct anti-SRBC PFC/Culture |
|---|---|---|
| 7a8MGuo | $3 \times 10^{-6}$ | $1850 \pm 70$ |
| 22827 (cinnamyl;11) | $3 \times 10^{-4}$ | $1357 \pm 226$ |
| 7m8oGuo | $3 \times 10^{-4}$ | $723 \pm 143$ |
| 24234 (benzyl;23) | $3 \times 10^{-5}$ | 2004 |
| 7a8oGuo | $10^{-5}$ | 1827 |
| 23643 (ethyl;6) | $3 \times 10^{-5}$ | $1009 \pm 97$ |
| 23644 (hexyl;4) | $3 \times 10^{-5}$ | $1058 \pm 154$ |
| 23894 (decyl;7) | $3 \times 10^{-6}$ | $90 \pm 15$[#] |
| 23643 (ethyl;6) | $3 \times 10^{-5}$ | $2067 \pm 230$ |
| 8BrGuo | $10^{-3}$ | $2450 \pm 325$ |
| 23369 (7-allyl-8-selenoxo;10) | $3 \times 10^{-5}$ | $2425 \pm 229$ |
| 7a8MGuo | $3 \times 10^{-4}$* | $925 \pm 80$ |

[1,2]See notes 1 and 2 of Table 1.
[3]The concentration providing the greatest number of plaques per culture in a given study is the value reported except where the symbol (*) is utilized to show that a supra-optional concentration was used.
[#]The peak number of PFC/culture shown was less than that of the control, thereby making the enhancement of PFC/culture effectively zero.

The results in tee above Table illustrate several points. First, the compounds of the present invention are more active than are the compounds disclosed in U.S. Pat. No. 4,643,992 with which they were compared. That improvement in activity was manifest either in a concentration at which peak adjuvanticity was observed (peak concentration) being about 0.5 to one log units (powers of ten) lower, or an adjuvanticity at a given peak concentration that was significantly higher, usually at least about 100 percent higher, than that exhibited for a compound of that patent.

The improved adjuvanticity can be seen in the first group of compounds in Table 5 where 7a8MGuo, 7m8oGuo and 7-cinnamyl-8-oxoguanosine (22827) were compared. Thus, 7a8MGuo was more than 100 percent more active than 7m8oGuo at two logs lower in concentration. 7-Cinnamyl-8-oxyguanosine was more than about 100 percent more active than 7m8oGuo at the same peak concentration. Similar results are shown near the bottom of Table 5 wherein 8-BrGuo was compared to 7-ethyl-8-oxoguanosine (23643) in which both compounds had similar numbers of plaques per culture, but the latter compound exhibited those values at a concentration 1.5 log units lower in concentration. (From other work to be discussed hereinafter, the result shown for 7-ethyl-8-oxoguanosine appears to be anomalously high.)

The substantially zero enhancement of PFC/culture exhibited by use of 7-decyl-8-oxoguanosine (23894) provides the basis for an $R^1$ radical being less than the length of a decyl radical.

The results shown in Table 6, below, were obtained similarly to those of Table 5, except that the immunostimulants of Table 6 had various further substituents on the ribosyl hydroxyl groups and some ring positions.

TABLE 6

Adjuvanticity Studies with Additional Ribosyl-substitution in the Murine System[1]

| Compound[2] | Peak Concentration[3] | Peak Direct anti-SRBC PFC/Culture |
|---|---|---|
| 23083 (21) | $10^{-4}$ | $2150 \pm 250$ |
| 7a8MGuo | $3 \times 10^{-5}$ | $1867 \pm 150$ |
| 23287 (18) | $10^{-4}$ | $1650 \pm 63$[4] |
|  |  | $1675 \pm 298$ |
| 8BrGuo | $3 \times 10^{-4}$ | $1167 \pm 68$ |
|  |  | $633 \pm 96$ |
| 23351[a] (21) | $10^{-4}$ | $1431 \pm 134$ |
| 23314[b] (19) | $10^{-5}$ | $243 \pm 19$ |
| 23350[c] (20) | $10^{-5}$ | $45 \pm 8$ |
| 7a8MGuo | $3 \times 10^{-5}$ | $1850 \pm 50$[a] |
|  | $3 \times 10^{-4}$* | $925 \pm 80$[b] |
|  | $3 \times 10^{-5}$ | $1975 \pm 109$[c] |
| 22360 (22) | $10^{-5}$ | $743 \pm 48$[5] |
| 8MGuo | $3 \times 10^{-4}$ | $527 \pm 25$ |

[1,2,3]See notes 1, 2 and 3 of Table 5, except that the 7-substituent name is omitted due to the presence of other substituents on the compounds, so that possible confusion with seemingly similar entries in other tables will be avoided.
[4]Two studies were carried out with the first number of each pair relating to a first study, and the second number of each pair relating to a second study.
[5]The value shown appears to be anomalously low in view of other data herein, e.g., see Table 8.
[a,b,c]Each of compounds 23351, 23314 and 25350 was compared to 7a8MGuo in separate studies. Results from each study are labeled with "a", "b" or "c" as appropriate.
*A supra-optimal amount of 7a8MGuo was used in study "b".

The results in Table 6 illustrate that a guanosine substituted at the 7- and 8-positions as before described can also be efficacious if its ribosyl hydroxyls bear substituent groups. Thus, a 7-allyl-8-thioxoguanosine whose 2'-and 3'-hydroxyls were bonded in an isopropylidene ring (23083) exhibited an activity substantially identical to that of 7a8oGuo, albeit at about one-half log higher concentration. Similarly, the 5'-acetyl ester of that isopropylidene derivative (23287) also exhibited a peak adjuvanticity that was about twice that exhibited by 8-bromoguanosine (8BrGuo), whose peak activity was at about one-half log higher in concentration.

A similar result was obtained when the 5'-acetyl (acetoxy) group was replaced by a benzoyl (benzoxy) group (23351). Interestingly, when an additional benzoyl group was added to compound 23351 at the 2-position amino group, the resulting compound (23350) was substantially inactive at the concentrations utilized in the studies.

When all three of the 2'-, 3'- and 5'-hydroxyls of the ribosyl group were acetylated (compound 22360), the compound maintained its high activity. Results shown in Table 8, hereinafter, indicate this tri-O-acetyl compound to be among the most active of all the compounds studied, particularly at low concentrations.

The results shown in Table 7, below, were obtained similarly to those discussed above, but using human lymphocytes. Some of those studies utilized lymphocytes from more than one individual, and are therefore reported with multiple entries.

TABLE 7

Adjuvanticity Studies in the Human System[1]

| Compound[2] | Peak Concentration[3] | Peak Direct anti-SRBC PFC/Culture |
|---|---|---|
| 7a8oGuo | $10^{-4}$ | $3038 \pm 288^a$ |
|  | $3 \times 10^{-4}$ | $9250 \pm 1010^b$ |
|  | $10^{-4}$ | $4831 \pm 270^c$ |
| 7m8oGuo | $10^{-3}$ | $1250 \pm 125^a$ |
|  | $10^{-3}$ | $830 \pm 67^b$ |
|  | $10^{-3}$ | $1225 \pm 175^c$ |
| 22360 | $3 \times 10^{-4}$ | $925^a$ |
| (22) | $3 \times 10^{-5}$ | $6008^b$ |
|  | $10^{-4}$ | $5050^c$ |
| 7a8MGuo | $3 \times 10^{-4}$ | $673^a$ |
|  | $10^{-4}$ | $6475^b$ |
|  | $10^{-4}$ | $3058^c$ |
| 7a8oGuo | $3 \times 10^{-4}$ | $477^a$ |
|  | $3 \times 10^{-4}$ | $10,313^b$ |
|  | $10^{-4}$ | $4413^c$ |
| 7m8oGuo | $10^{-3}$ | $528^a$ |
|  | $10^{-3}$ | $297^b$ |
|  | $10^{-3}$ | $263^c$ |
| 7m8oGuo | $3 \times 10^{-4}$ | $5775 \pm 214$ |
| 23643 (ethyl;6) | $3 \times 10^{-4}$ | $9045 \pm 310$ |
| 7a8oGuo | $3 \times 10^{-4}$ | $11,938 \pm 762$ |
| 23644 (butyl;2) | $3 \times 10^{-4}$ | $12,238 \pm 150$ |
| 23369 (7-allyl-8-selenoxo;10) | $3 \times 10^{-4}$ | $2204 \pm 370$ |
| 23644 (butyl;2) | $3 \times 10^{-4}$ | $3371 \pm 120$ |
| 23679 (butenyl;3) | $3 \times 10^{-4}$ | $3129 \pm 252$ |
| 7a8oGuo | $3 \times 10^{-4}$ | $4079 \pm 102$ |
| 22827 (cinnamyl;11) | $3 \times 10^{-4}$ | $2577 \pm 300$ |
| 7a8oGuo | $3 \times 10^{-4}$ | $7075 \pm 260$ |
| 7m8oGuo | $10^{-3}$ | $780 \pm 142$ |

[1,2,3]See notes 1, 2 and 3 of Table 5, except that the name of the 7-substituent is omitted where sugar ring substituents are also present.
[a,b,c]Compounds were compared using lymphocyte preparations from three persons designated a, b and c. Compound comparisons are therefore made within a given lymphocyte preparation. The results labeled "a" are compared with themselves, as are those labeled "b" and those labeled "c".

The results in Table 7 again show the enhanced efficacy of compounds of the present invention as compared with 7-methyl-8-oxoguanosine in the human system. Those results also illustrate the preference for 7-position substituents that are shorter in length than a hexyl group. Thus, although the 7-cinnamyl-8-oxoguanosine (22827), which is longer than a hexyl group, was quite active relative to 7m8oGuo, it was substantially less active than 7a8oGuo.

The similarity in adjuvanticity of 7a8oGuo, 7-butyl-8-oxoguanosine (23644), and 7-(2-butenyl)-8-oxoguanosine (23679) all of whose 7-substituents are shorter than a hexyl group and longer than an ethyl group is also illustrated. Similarly, the enhanced adjuvanticity of compounds having a 7-substituent longer than an ethyl group is seen by a comparison of the adjuvanticity of 7-ethyl-8-oxoguanosine (23643) with that of either 7a8o-Guo or 7-butyl-8-oxoguanosine (23644).

The adjuvanticity differences between the particularly preferred compounds of this invention, whose R[1] radicals are longer, than ethyl and shorter than hexyl and whose ribosyl groups are unsubstituted, and 7m8o-Guo and 7-ethyl-8-oxoguanosine can be seen from the results in Table 8, below. Those results came from a larger, single study carried out using murine lymphocytes and nine guanosine derivatives in which the guanosine derivative was contacted with the lymphocytes at the relatively low concentrations that are desirable for use. These results are shown in Table 8 below.

TABLE 8

Low Concentration Adjuvanticity Studies in the Murine System[1]

| Compound[2] | Direct anti-SRBC PFC/Culture at[3]: | |
|---|---|---|
|  | $7.5 \times 10^{-6}$ M | $1 \times 10^{-5}$ M |
| 23924 (hexyl;4) | 103 | 243 |
| 7m8oGuo | 128 | 145 |
| 23644 (butyl;2) | 292 | 900 |
| 23643 (ethyl;6) | 313 | 270 |
| 23679 (2-butenyl;3) | 383 | 612 |
| 24069 (propyl;5) | 793 | 1306 |
| 7a8oGuo | 1028 | 1387 |
| 7a8MGuo | 1130 | 1049 |
| 22360 (22) | 1391 | 1176 |
| Control (antigen ± no nucleoside) | 57 |  |

[1,2]See notes 1 and 2 of Table 5, except as to compound 23360 (7-allyl-8-thioxo-2',3',5'-triacetoxyguanosine).
[3]Concentrations of compounds in moles per liter (M).

Examination of Table 8 reveals that 7-hexyl-8-oxoguanosine (23924) is about equally active compared to 7m8oGuo at the lower concentration, and about twice as active at the higher concentration. The 7-butyl-(23644), 7-ethyl-(23643), and 7-(2-butenyl)-8-oxoguanosines all are at least about twice as active as 7m8oGuo at the lower concentration, with the 7-butyl- and 7-(2-butenyl)-8-oxoguanosines exhibiting about 100 to about 200 percent enhancements in adjuvanticity over 7-ethyl-8-oxoguanosine at the higher concentration.

The 7-propyl-8-oxoguanosine (24069) and 7a8oGuo, as well as 7a8MGuo and its 2',3',5'-triacetyl derivative (22360) were all several times more active as adjuvants than was 7-ethyl-8-oxoguanosine, and still more active when compared with 7m8oGuo.

A plot of the value (PFC-control PFC) per micromole data of Table 8 for the 7-substituted-8-oxoguanosines at the higher concentration of that Table versus the length of the longest carbon atom chain in the substituent, taking allyl to be slightly longer than propyl, and 2-butenyl to be slightly longer than butyl, is shown in FIG. 5, and illustrates the relation between adjuvanticity and chain length. As can be seen, the adjuvanticity peaks at a chain length between about 3 to about 4 carbons with substantially lower activities being exhibited by substituents shorter than three carbons; i.e., methyl and ethyl. The hexyl radical substituent exhibits a similar activity to those of methyl and ethyl radicals.

This finding of an apparent structure activity relationship based on the approximate chain length of the 7-substituent was quite surprising. R. Gallo, in *Progress in Physical Organic Chemistry*, vol. 14, R. Taft, ed., John Wiley & Sons, N.Y., (1983) pages 115–163, discussed quantitative structure activity relationships, and reported several free energy relations in biological systems that were linear using the Taft Es parameter. The Es parameter is said to provide a relative free energy for steric effects.

For example, the Gallo paper reported that others had reported a linear, Es correlation for acylation and deacylation of alpha-chymotrypsin, the metabolism of primary alcohols to glucuronides in rabbits, locomotor activity of amphetamines in mice, in inhibition of cholinesterase by diethyl substituted phenyl phosphates, in phenoxy ethylcyclopropylamine monoamine oxidase inhibitor and in diphenylhydramine antihistamines, as well as in the action of tuberculostatic drugs of the isonicotinic acid hydrazide type. (See, Gallo at page 125.)

Thus, it might have been expected that a similar correlation would be found for the 7-substituents of a guanosine in the present situation using either Es or its correlative steric parameter nu that is said to be based on Van der Waals radii and was developed by Charton, J. Am. Chem. Soc., 97:1552–1556 (1975). However, an examination of nu and Es values for straight chain 7-hydrocarbyl substituents such as propyl, butyl, pentyl and octyl shows that the nu values are all 0.68 for those substituents, whereas the Es values are −0.36, −0.39, −0.40 and −0.33, respectively. It is quite apparent that the PFC/culture results of Table 8 when plotted against either nu or Es would not be linear, nor would any correlation be shown between the results and those steric parameters.

It is noted further that Charton [J. Org. Chem., 41:2217–2220 (1976)] also reported a nu value of 0.68 for the straight chain $C_9$, $C_{11}$, $C_{13}$, $C_{15}$ and $C_{17}$ alkyl radicals, which would imply that a 7-butyl radical and a 7-decyl radical should provide similar PFC/culture if the adjuvanticity studied herein were correlatable as were the other previously mentioned biological processes. However, even when one compares the substantially zero adjuvanticity exhibited by 7-decyl-8-oxoguanosine (23894) with the moderately active 7-ethyl- and 7-hexyl-8-oxoguanosine derivatives (23643 and 23644, respectively) of Table 5 whose nu parameters are 0.56 and 0.73, respectively, it is again very apparent that the adjuvanticity enhanced by a compound of this invention does not correlate with nu or its correlative, Es, parameter, nor can that adjuvanticity be predicted by either parameter.

Still another unexpected property of the more preferred compounds; i.e., where $R^1$ is longer than ethyl and shorter than hexyl and where the ribosyl group is unsubstituted, is that the dose-response curve is broader near the peak concentration than is a similar curve obtained for 7m8oGuo. This broadened response is not seen from the single-valued Tables above.

In some instances, the added breadth appears toward concentrations lower than that of the peak concentration and in others it appears at higher concentrations than the peak concentration. This apparent skewing of the dose-response curves is most likely a function of varying the concentration of nucleoside used in the studies in one-half log units.

Regardless of the reason for the apparent skewing of the dose-response curves, a measure of relative breadth can be obtained by summing the average number of plaques (PFC/culture) found at one-half log intervals within one log concentration unit of the peak concentration, including the PFC/culture at the peak concentration. The obtained sum is then divided by three (the number of values summed) to provide the average 1 log plaque value. That average 1 log plaque value can thus be obtained from the average peak value plus average values one-half log on either side of the peak concentration, or from the average peak value plus the average values obtained from the concentration one-half log higher and one log higher (or one-half log lower and one log lower) than the peak concentration. Average plaque values are selected to provide the largest sum, and the background value where SRBC alone were present is subtracted from each value prior to its being summed. Each value is divided by the number of micromoles of nucleoside present in culture, the three largest values obtained in the 1 log range are summed, and divided by three to yield the average 1 log per micromole.

When calculations such as those above are carried out and averaged for various otherwise unrelated studies using a particular guanosine derivative, one finds that the average 1 log plaque values per micromole for the more preferred compounds of this invention are much greater than is the value for 7m8oGuo. These differences in values are found when data from both human and murine lymphocyte systems are examined. Representative values are illustrated in Table 9, below.

TABLE 9

| Compound[2] | Average 1 Log Plaque Values[1] | |
|---|---|---|
| | Murine[3] | Human[3] |
| 7a8oGuo | 98,237 ± 42,041 | 22,640 ± 4187 |
| 24234 (benzyl;23) | 110,777 ± 42,823 | — |
| 7a8MGuo | 326,840 ± 170,907 | 45,630 ± 28,808 |
| 7m8oGuo | 22,359 ± 5154 | 867 ± 217 |
| 23644 (butyl;2) | 118,886 ± 80,092 | 52,397* |
| 23679 (2-butenyl;3) | 52,332* | — |
| 22360 (22) | 53,695 ± 28,444 | 38,508 ± 26,802 |

[1]Values were obtained as described above.
[2]See note 2 of Table 1.
[3]Murine = murine lymphocyte system as described for Tables 1, 4, 5, 6 and 8. Human = human lymphocyte system as described for Tables 3 and 7.
*Value obtained from a single study.

A dose response curve can be too narrow and thereby not permit appropriate dosing of a particular recipient. For example the data for the human system shown in Table 7 illustrate differences of as much as a factor of three to ten (one-half to one log unit) in the peak concentration of the compounds studied when lymphocyte preparations from three different individuals were compared. If the dose-response curve were too narrow, a selected dosage usual for recipients generally could be too high or too low for a particular recipient. Thus, the broadened dose-response curves for the more preferred compounds herein offer a further advantage compared to 7m8oGuo. The data of Table 9 show average 1 log plaque values in the human system to be about 25 to about 60 times greater for the more preferred compounds than 7m8oGuo.

A further structure activity profile similar in shape to that shown in FIG. 5 can be obtained using peak PFC/culture data for the same guanosine and additional derivatives taken from several studies. Here, a single peak PFC value for each study is used. That value is obtained by dividing the PFC per culture values obtained by the number of micromoles of guanosine present in the study that provided PFC value, after subtracting the background plaques of a control from the study. Peak values so obtained for each study using a given compound are then averaged to diminish fluctuations in response from study to study, as was noted to occur previously.

A plot of such averaged peak values for the murine system is shown in FIG. 6, whose abscissa positions were determined as recited for FIG. 5. The average peak values shown in FIG. 6 are not as precise as are those of FIG. 5 due to the response fluctuations observed between the several studies utilized for their derivation. In addition, several points on the graph are a result of single studies or two studies that provided widely varying results. For example, the average peak value for 7-butyl-8-oxoguanosine (23644) obtained from two very different peak values appears to be anamolously high in view of the data of Table 8 for the murine system and of Table 7 for the human system. Thus, the hydrocarbyl substituent providing the greatest peak PFC/culture value appears to be one to two carbon atoms longer in FIG. 6 than in FIG. 5. Nevertheless, the trend in the structure activity relation shown in the graph of FIG. 6 is substantially similar to that shown in FIG. 5, whose data are believed to be precise and directly comparable, thereby lending credence to the results shown in FIG. 6. Those substantially similar results show that $R^1$ radicals longer than ethyl but shorter than about hexyl provide substantially, and unpredictably, enhanced adjuvanticity as compared to 7m8oGuo.

Not only does 7a8oGuo exhibit unexpectedly high adjuvanticity at a lower peak concentration than does 7m8oGuo, and exhibit a broadened dose-response curve, 7a8oGuo also is unexpectedly more soluble in human urine than is 7m8oGuo. That unexpectedly high solubility in urine is contrary to the predicted solubility in water based upon calculated pi constant values. Urine was used in solubility studies as compounds of this invention are for the most part eliminated via the urine from the bodies of animals to which they administered. Insolubility in urine can lead to precipitation of the compound in the kidney with subsequent damage to that organ.

Pi constant values are a measure of relative solubility in 1-octanol and in water as determined by partition coefficients between the two solvents. The pi constant value is said to be the parameter of choice for correlating both binding to biological macromolecules and transport through a biological system. Norrington et al., *J. Med. Chem.*, 18, 604 (1975).

The pi constant parameters were developed by Leo and Hansch and their co-workers. See, for example, Leo et al., *Chem. Rev.*, 71, 525 (1971), and C. Hansch and A. Leo, *Substituent Constants for Correlation Constants in Chemistry*, Wiley Interscience, N.Y., 1979.

A pi constant value, usually shown using the Greek letter, $(\pi)$ is calculated using the equation:

$$\pi = \log P_x - \log P_H$$

where $P_x$ is the partition coefficient for the compound of interest and $P_H$ is the partition coefficient for the corresponding unsubstituted compound. Once a series of pi constant values is obtained for a group of substituents for otherwise related compounds, they can be used for other, unrelated compounds bearing those substituents without having to carry out the partition studies for those unrelated compounds. Hydrogen as a substituent is given a value of zero.

As can be determined from examination of the above equation, substituents that provide greater solubility in water lead to pi constant values that are relatively more negative. Conversely, substituents that provide greater 1-octanol solubility lead to pi constant values that are relatively more positive.

Pi constant values found in the Hansch and Leo book, above, are 0.56 for a methyl radical and 1.10 for an allyl radical. Thus, a compound bearing an allyl radical is predicted to be more soluble in 1-octanol than is a similar compound bearing a methyl radical. Conversely, the presence of a methyl radical on a given compound would be expected to lead to greater water solubility for that compound as compared to a similar compound having an allyl radical in place of the methyl radical.

Using the LSE option of the ChemLab computer program to calculate log P values from the pi constant values above, and then calculating pi constant values for 7m8oGuo and 7a8oGuo, the values for log $P_x$ are $-8.43$ and $-7.46$, respectively, where x is methyl or allyl, respectively. The computer program utilizes the formalism of R. F. Rekker, *The Hydrophobic Fragment Constant*, Elsevier, N.Y. (1977) Thus, again, use of the pi constant, predicts a greater water solubility for 7m8oGuo than for 7a8oGuo.

When solubility studies in human urine for 7m8oGuo and 7a8oGuo were carried out, solubilities of 4.88 mg/ml and 16.3 mg/ml, respectively were found. Thus, 7a8oGuo possessed about a three-fold greater solubility than did 7m8oGuo, but was predicted from a pi constant analysis to be less soluble. Solubilities in urine could be expected to be lower than those for water due to the relatively higher salt content in urine than is found in water.

A pi constant analysis for 7a8MGuo or other compounds disclosed herein has not been undertaken. The above solubility study using human urine included 7a8MGuo, and that compound was found to be relatively insoluble (0.30 mg/ml) as would be expected from the presence of its sulfur atom.

The above solubility studies were carried out by shaking an excess of each compound in human urine at 37° C. for a time period of about 18 hours; sample containers were flushed with argon gas prior to admixture. Each sample was filtered through a 5 micron pore-sized filter, diluted as necessary with the HPLC mobile phase, and then quantified by HPLC.

D. T Cell-Replacing Activity

Figure 1:
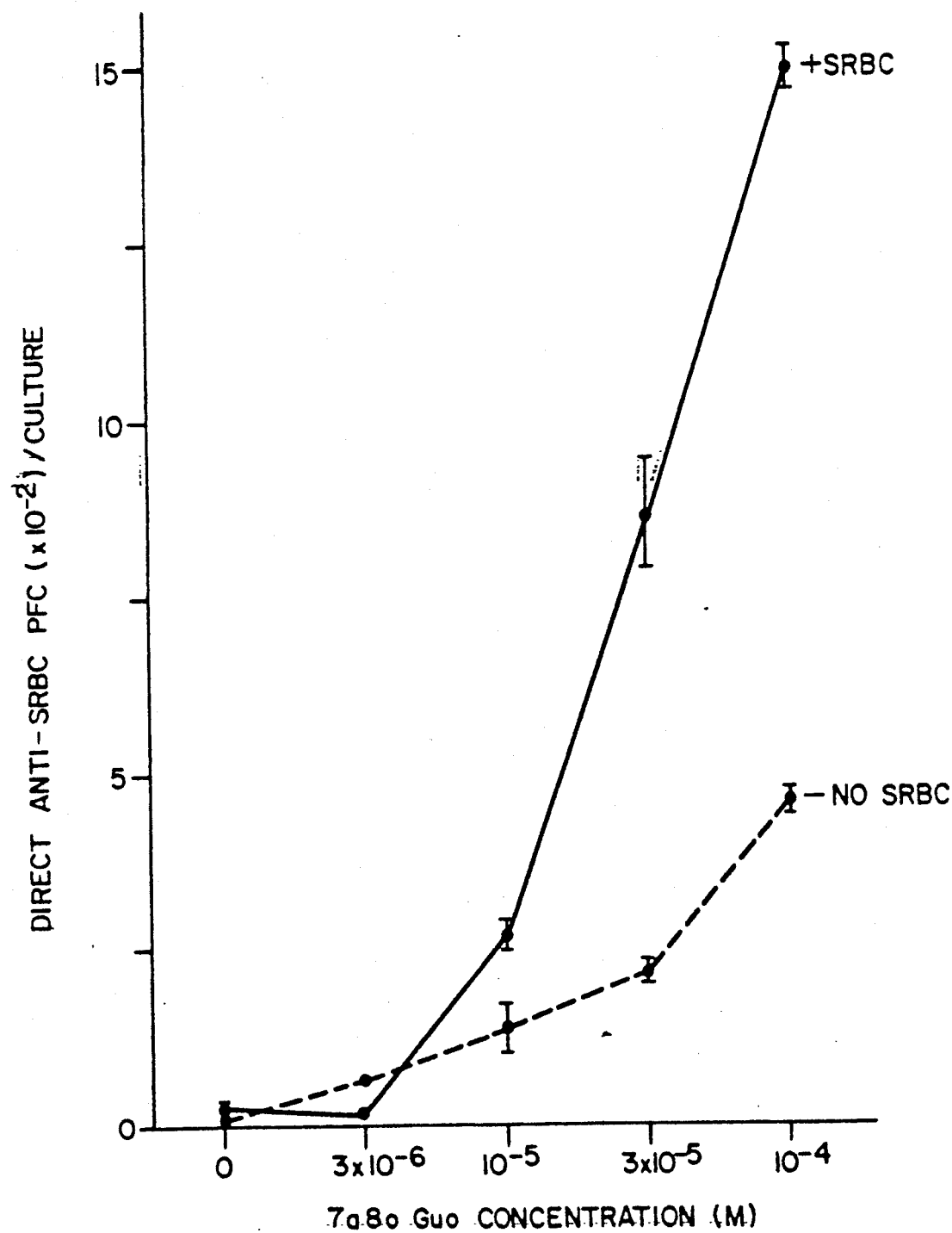
FIG. 1 is a graph that illustrates the T cell-replacing activity of an aqueous composition containing 7-allyl-8-oxoguanosine (7a8oGuo) used to contact CBA/CaJ mouse B cell cultures depleted of T cells but which cultures contained sheep red blood cells (SRBC) as a specific antigen. The points of the solid line illustrate plaque formation in the presence of incremental amounts of 7a8oGuo with a constant amount of SRBC present in the culture. The dashed lie represents results in the absence of SRBC. The ordinate is in units of direct anti-SRBC plaque forming cells (PFC) times $10^{-2}$ per culture. The abscissa is in units of concentration (molarity, M) of 7a8oGuo present in the contacting composition. Further details are provided hereinafter.

The ability of the compositions of this invention to substitute for T cells in the antibody response to a T-dependent antigen is illustrated in FIG. 1. Here, B cells generated in vitro by treatment with monoclonal anti-thy 1.2 plus complement were cultured with or without SRBC as antigen in the presence of compositions containing incremental concentrations of 7a8oGuo.

The data of FIG. 1 illustrate that under these conditions isolated B cell cultures responded poorly to antigen unless supplemented with 7a8oGuo. The 7a8oGuo modulated response was dose-dependent as well as antigen-dependent. In addition, this response cannot be attributed to non-specific polyclonal activation of B cells because omission of antigen diminished the response markedly (dashed line); the response of normal spleen cells to SRBC ranges from about 200 to about 600 PFC per culture.

The data of FIG. 1 illustrate that that contacting B cells in vitro with a composition of this invention provides a T cell-like signal to those contacted cells. Those results also show that the result is antigen-specific and dose-dependent as to the guanosine nucleoside derivative.

E. In Vitro Reconstitution of the Primary Humoral Immune Response

The B cells used for the data of FIG. 1 were immunocompetent, and obtained from CBA/CaJ mice. CBA/N mice possess an x-chromosome linked (x-linked) primary B cell immunodeficiency, and thereby can provide a murine model for sex-linked immunodeficiency.

The CBA/N strain is thought to be deficient in the functional activity of a subpopulation of mature B lymphocyts bearing the Lyb 3/5/7 antigens. See, Huber et al., *J. Exp. Med.*, 145:1(1977); Ahmed et al., *J. Exp. Med.*, 145:101 (1977); and Subbaro, *J. Immunol*, 122:2279 (1979).

Cultures of spleen cells from male and female homzygous CBA/N and male mice heterozygous for the CBA/N gene, called the xid gene, (male mice bear the X chromosome) was prepared as described in the Materials and Methods Section. 0.1 Milliters of a 0.1 percent (v/v) SRBC suspension alone or the SRBC suspension plus incremental amounts of 7a8oGuo were added to the cultures, using $5 \times 10^6$ cells/ml. Direct anti-SRBC plaque-forming cultures per culture were assessed after 4 days of culture.

Figure 2:
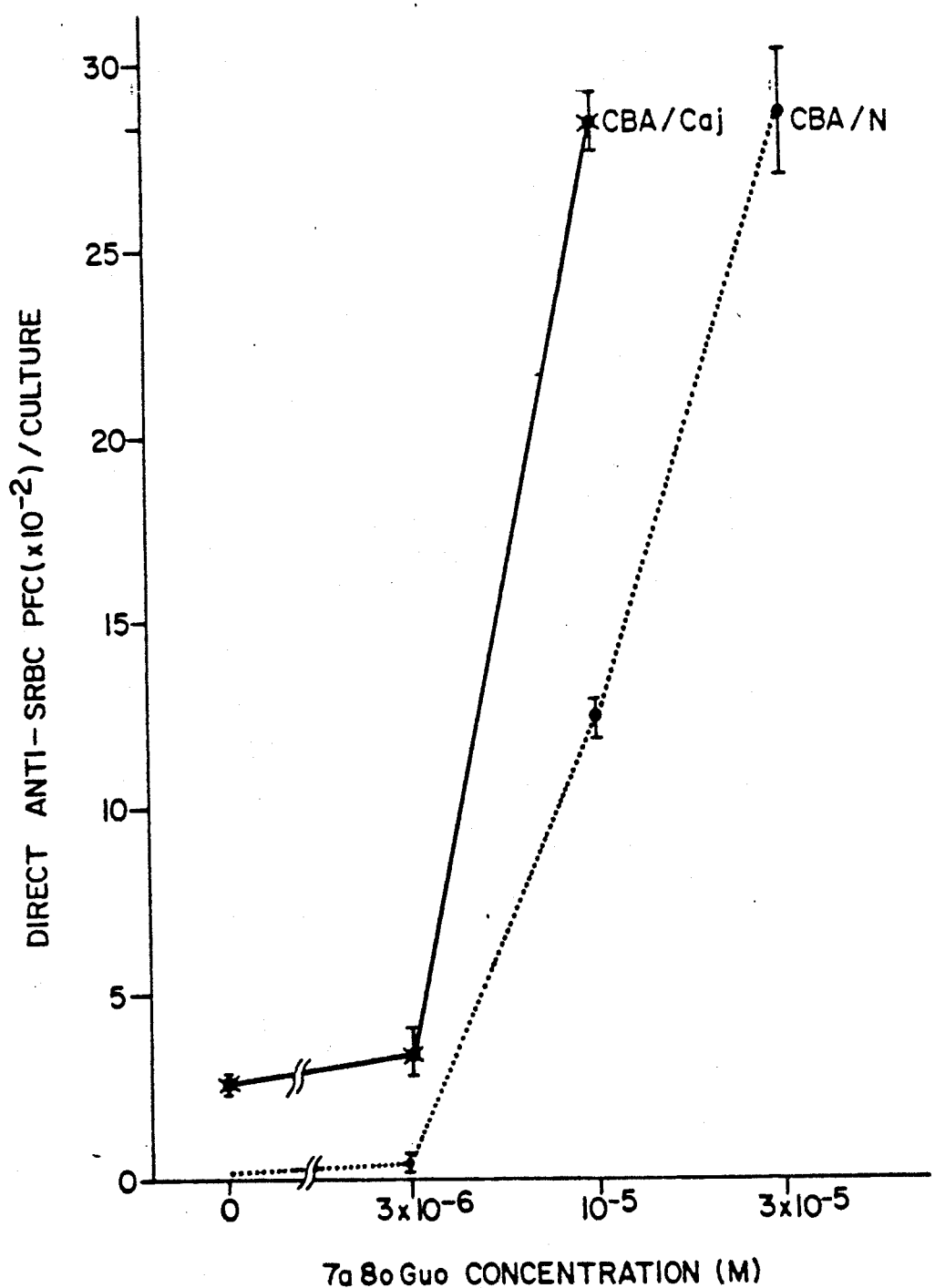
FIG. 2 is a graph that illustrates the in vitro reconstitution of the primary humoral immune response to a specific antigen, SRBC, in cultured immunodeficient CBA/N mouse spleen cells (dotted line) obtained by contacting those cells with an aqueous composition containing 7a8oGuo, in the further presence of SRBC. A similar study using spleen cells from immunocompetent CBA/CaJ mice (solid line) is also shown in the graph for comparison. The points on each line represent the PFC value obtained in the presence of the indicated amount of 7a8oGuo plus SRBC. The ordinate and abscissa are as in FIG. 1. Further details of this study are provided hereinafter.

The results of this study comparing cells from CBA/N mice with a preparation of spleen cells from CBA/CaJ mice, are shown in FIG. 2. Examination of FIG. 2 at the zero guanosine derivative concentration level shows substantially no response, as compared to about 250 PFC/culture for the immunocompetent CBA/CaJ cells.

Further examination of the Figure shows that both the immunocompetent CBA/CaJ cells and originally immunoincompetent CBA/N cells were made capable of producing about the same number of PFC/culture in the presence of 7a8oGuo. Surprisingly, those similar values were obtained by contacting the cells with compositions containing only a one-half log difference in concentration of 7a8oGuo, $10^{-5}$ M vs $3 \times 10^{-5}$ M for CBA/CaJ and CBA,/N cells, respectively.

The data of FIG. 2 thereby illustrate that contacting x-linked immunodeficient splenocytes with a composition of this invention could reconstitute the primary humoral immune response to SRBC of those otherwise immunodeficient cells.

Immunodeficiency in mice as well as other mammals can come from old age or senescence as well as by genetic defect as discussed above in relation to FIG. 2. Thus, animals that were immunocompetent as juveniles or adults can become immunodeficient as they reach old age. That is the case for the inbred CBA/CaJ mouse strain.

A further study of the reconstitution of a primary humoral antibody response to SRBC was carried out using spleen cells from senescent, 156-week old, CBA/CaJ mice that had become immunodeficient through age. The in vitro responses of those spleen cells to SRBC in a plaque-forming assay were compared to similar responses from another group of healthy, adult 8-week old, CBA/CaJ mice. This comparison was carried out as described before in relation to FIG. 2, again using a composition containing 7a8oGuo to contact the splenocytes. The results are shown in FIG. 3.

Figure 3:
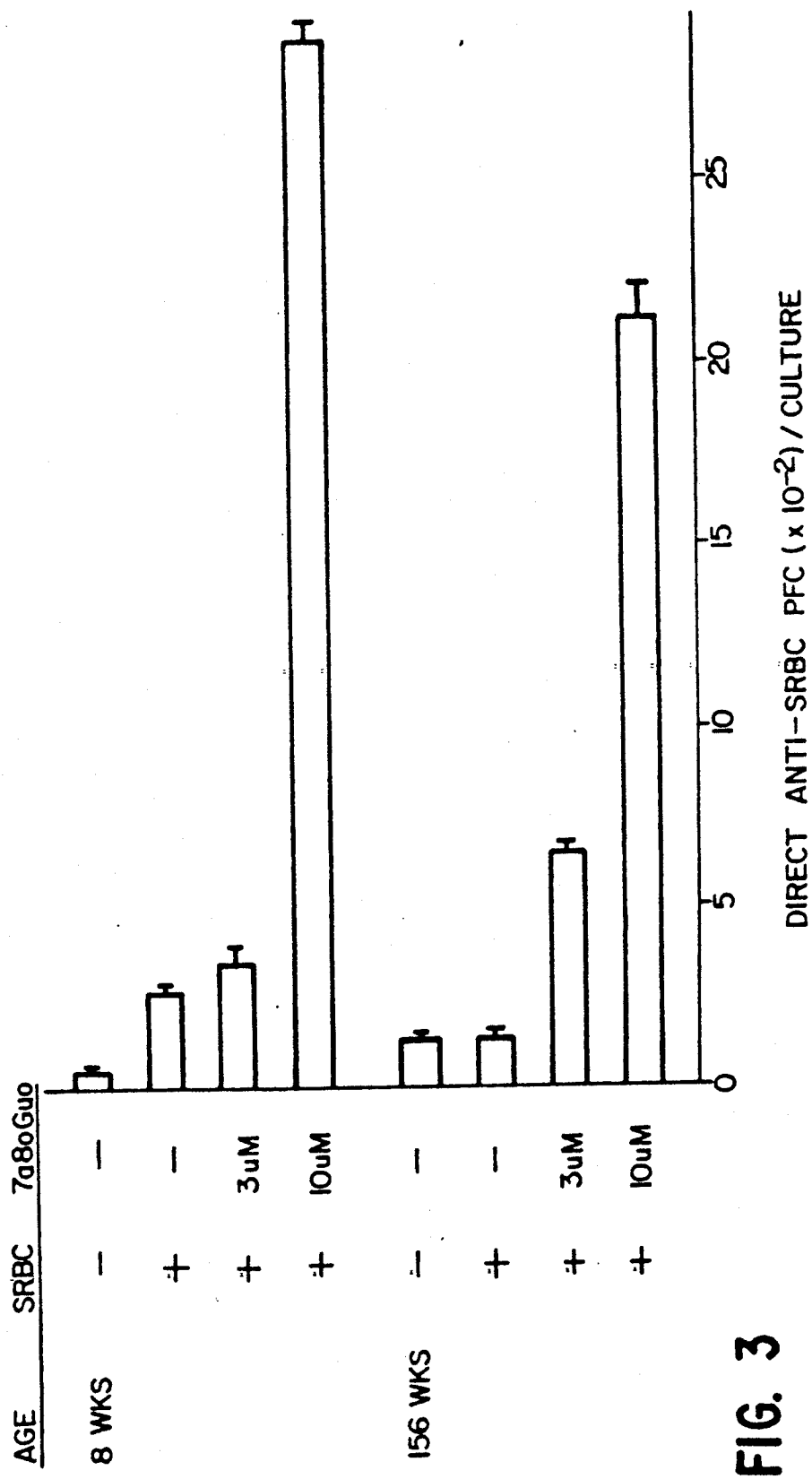
FIG. 3 shows bar graphs that illustrate the in vitro reconstitution of the primary humoral immune response to SRBC in immunodeficient senescent (156 weeks old) CBA/CaJ mouse splenocytes as compared to splenocytes from immunocompetent (8 weeks old) CBA/CaJ mice obtained by contacting those cells with an aqueous composition containing 7a8oGuo. The left portions indicate the age in weeks (wks) of the mice from which the cells were obtained, the presence (+) or absence (−) of SRBC, and the absence (−) or micromolar (um) concentration of 7a8oGuo. The bar lengths are in the same units as the ordinates of FIGS. 1 and 2. Further details of this study are discussed hereinafter.

As can be seen from an examination of FIG. 3, the PFC/culture for the healthy adult mice controls containing SRBC but no guanosine derivative were several times the number formed in the absence of both SRBC and guanosine. The PFC/culture for the controls for the senescent mice were usual for such mice, being about equal for both, and elevated compared to those of healthy adult. Those relatively elevated and similar responses are thought to be due to the formation of autoantibody-producing clones.

Further study of the Figure shows a guanosine derivative dose-related response to SRBC in the presence of both 3 and 10 micromolar (uM) concentrations of 7a8oGuo. That response was observed for both the immunocompetent healthy adult splenocytes and the previously immunodeficient, but now primary humoral response-reconstituted senescent splenocytes.

The results shown in FIG. 3 thereby illustrate that contacting immunodeficient senescent splenocytes with a composition of this invention can reconstitute this deficient immune response. The data of FIGS. 2 and 3 illustrate that reconstitution in both an X-linked and an age-linked immunodeficiency.

F. In Vivo Antibody Responses

CBA/CaJ mice were immunized intraperitonally (i.p.) using a conjugate (TNP-BSA) prepared by the reaction of 2,4,6-trinitrobenzene sulfonic acid (TNBS) and bovine serum albumin (BSA) in a 0.28 molar cacodylate buffer, at pH 6.9. Each animal received an intraperitoneal (i.p.) injection containing 50 micrograms (ug) of the immunizing conjugate. One group of mice thereafter (within about 30 minutes) received another i.p. injection that contained 7a8MGuo in either 100 percent sesame seed oil or an aqueous composition conaining 2 volume percent sesame oil sonicated with saline. Each animal received 0.2 ml of the compositions each of whose concentrations of 7a8MGuo was 5 mg/ml. A third group of mice received the immunization but no composition of this invention and served as a control. Anti-TNP-BSA antibody secretion from each group was thereafter monitored over a period of 37 days by standard enzyme-linked immunosorbant assay (ELISA) techniques using TNP-BSA as antigen.

Figure 4:
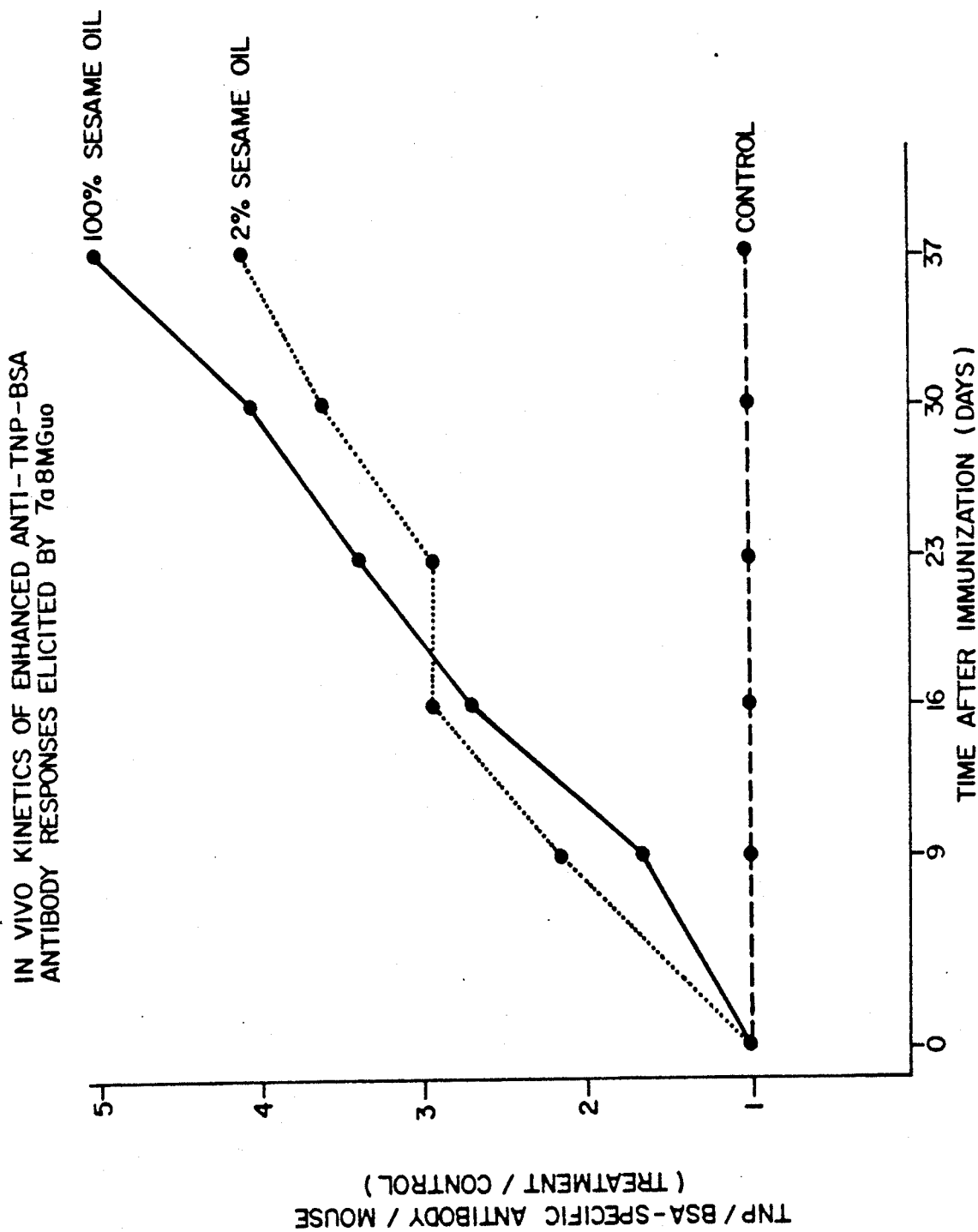
FIG. 4 is a graph containing a number of plots that illustrate the in vivo kinetics of enhanced anti-trinitrophenyl bovine serum albumin (TNP-BSA) antibody responses elicited by contacting leukocytes in vivo with a composition containing 7-allyl-8-mercaptoguanosine (7a8MGuo). Here, the guanosine derivative (0.2 ml of 7a8MGuo at 5 mg/ml) was in a vehicle of 100 percent sesame oil (solid line) or 2 percent sesame oil in saline (dotted line) when introduced into the animal.

The results of this study are shown in FIG. 4, and are illustrated as a ratio of the ELISA antibody titers obtained using either of the 7a8MGuo-containing compositions to the control titer. As can be seen from FIG. 4, use of a composition containing77a8MGuo caused the anti-TNP-BSA antibody titers to be greater than the controls from the first day titers were measured (day 9 after administration) through the end of the study (37 days post administration).

A feature not shown by FIG. 4 is that the control antibody level peaked at a time about two weeks after administration and then began to diminish. Contrarily, the antibody titers for animals that received 7a8MGuo increased through a time about two weeks after administration, and thereafter remained at about the same elevated level for the duration of the study. Thus, after the data points taken two weeks into the study, the data of FIG. 4 illustrate the relative constancy of the antibody titers after administration of 7a8MGuo and the falling titers of the controls.

G. T Helper Cell Activation

T Lymphocytes activated by foreign or modified self major histocompatibility complex (MHC) determinants are considered to represent crucial effector cells involved in the control of self integrity; allograft rejection and elimination of virally or chemically altered self structures represent clinical examples of this defense mechanism. T cell proliferation in the presence of an alloantigen can provide a correlation to T helper activity, and its enhancement. Pobor et al., *Scan. J. Immunol.* 18:207-215 (1983). T cell proliferation studies in the presence of an alloantigen and in the further presence or absence of a guanosine derivative of this invention were therefore carried out, and are discussed hereinafter.

In evaluating the effect of a guanosine derivative on alloantigen-induced proliferation, it is imperative to minimize the simultaneous mitogenic response of B cells to contact with a guanosine derivative. Spleen cells from SJL mice (whose B cells are hyporesponsive to the mitogenic effect of a guanosine derivative, but not to its adjuvant activity) were used as responder cells in two studies. Those responder cells were stimulated with irradiated allogenic cells (from CBA/CaJ mice) in the presence of no added nucleoside, incremental amounts of a guanosine derivative of the invention, 7M8oGuo, or with another guanosine derivative, 8MGuo, used as a positive control.

A third and fourth study utilized thymocytes from CBA/CaJ mice as the stimulated (responder) cells, and irradiated BDF$_1$ mouse spleen cells as the stimulator cells. Two guanosine derivatives of the present invention, 7a8MGuo and 7a8oGuo, were used for these studies, with 8MGuo serving as positive control for one of the studies.

Thymocytes are largely immature T cells that do not respond vigorously to allogeneic cells. However, in the presence of interleukin-2 (IL-2), those cells develop responsiveness to allogeneic stimulation. The present studies utilizing thymocytes were therefore carried out in the presence of a co-stimulating amount of IL-2.

The results of the four T cell proliferation studies are shown in Table 10, below. Each of those studies utilized separate cell populations, so the results are best compared only with each study.

TABLE 10

| Responder Cells[2] | T Cell Proliferation in Mixed Leukocyte Cultures[1] | | |
|---|---|---|---|
| | Irradiated Stimulator Cells[3] | Nucleoside[4] | [³H]TdR Uptake[5] |
| Study 1 | | | |
| SJL Splenocytes | CBA/CaJ Splenocytes | | |
| + | − | — | 21,600 ± 900 |
| + | − | 10$^{-5}$(7a8MGuo) | 36,700 ± 2400 |
| − | + | — | 1300 ± 50 |
| − | − | 10$^{-5}$(7a8MGuo) | 300 ± 110 |
| + | + | — | 40,100 ± 2300 |
| + | + | 10$^{-5}$(7a8MGuo) | 67,500 ± 2900 |
| + | + | 10$^{-3}$(8MGuo) | 28,100 ± 2700 |
| Study 2 | | | |
| SJL Splenocytes | CBA/CaJ Splenocytes | | |
| + | − | — | 16,600 ± 1100 |
| + | − | 10$^{5}$(7a8MGuo) | 19,100 ± 1100 |
| − | + | — | 500 ± 30 |
| − | − | 10$^{-5}$(7a8MGuo) | 2300 ± 200 |
| + | + | — | 16,500 ± 1300 |
| + | + | 10$^{-5}$(7a8MGuo) | 36,400 ± 3800 |
| + | + | 10$^{-3}$(8MGuo) | 30,800 ± 1300 |
| Study 3 | | | |
| CBA/CaJ Thymocytes | BDF$_1$ Splenocytes | | |
| + | − | — | 3,100 ± 300 |
| − | + | — | 300 ± 70 |
| + | + | — | 12,500 ± 90 |
| + | + | 10$^{-6}$(7a8MGuo) | 11,800 ± 400 |
| + | + | 10$^{-5}$(7a8MGuo) | 15,300 ± 600 |
| + | + | 10$^{-4}$(7a8MGuo) | 21,400 ± 1200 |
| + | + | 10$^{-5}$(8MGuo) | 15,600 ± 1000 |
| + | + | 10$^{-4}$(8MGuo) | 13,800 ± 1000 |
| Study 4 | | | |
| CBA/CaJ Thymocytes | BDF$_1$ Splenocytes | | |
| + | − | — | 780 ± 70 |
| − | + | — | 300 ± 60 |
| + | + | — | 5400 ± 200 |
| + | + | 10$^{-6}$(7a8oGuo) | 8300 ± 300 |
| + | + | 10$^{-5}$(7a8oGuo) | 8000 ± 300 |
| + | + | 10$^{-4}$(7a8oGuo) | 10,000 ± 800 |

[1] Plus signs (+) are utilized to indicate the presence of the material of the column heading in the culture medium, whereas minus signs (−) are utilized to show absence of such a material from the culture medium. Details of the procedures and culture media utilized are provided in the Materials and Methods Section.
[2] Cells whose proliferation was assayed.
[3] Allogeneic cells used to co-stimulate proliferation, after exposure to 2500 rad.
[4] Nucleoside concentrations are in molarity multiplied by the number in the column. Parenthesized abbreviations 7a8oMGuo, 7a8oGuo and 8MGuo are as described elsewhere herein.
[5] [³H]TdR uptake in counts per minute.

The results shown in the above Table illustrate that contacting T cell-containing responder populations with a composition of this invention in the presence of allogeneic stimulator cells causes enhanced proliferation of those responder cells. That induced T cell proliferation was in excess of the proliferation effect caused by the allogeneic cells themselves when the guanosine nucleoside derivative was absent. Still further, intrastudy comparisons of the effects found using a compound of this invention as compared to a previously known compound, 8MGuo, generally showed an unexpected enhancement when a compound of the present invention was used.

Having generally described this invention, a further understanding can be obtained by reference to syntheses and procedures that are provided hereinafter below for purposes of illustration.

VIII. Materials and Methods

A. Syntheses

EXAMPLE 1

General Procedure for Preparation of 7-hydrocarbyl-substituted-8-oxoguanosines

1-Amino-8-oxoguanosine (hereinafter Compound A) served as a starting material for several syntheses using a two-step procedure. That material was prepared essentially by the method described in Rizkalla et al., *Biochim. Biophys. Acta.*, 195: 285-293 (1969).

Step 1

To a solution of Compound A [9.5 grams (g), 30 millimoles (mM)] in dimethyl formamide (DMF) was added sodium methoxide (33 mM) in 250 milliliters (ml) of DMF. The reaction mixture was stirred at ambient room temperature (about 18°-22° C.) for 30 minutes. A DMF solution (10 ml), containing the alkylating agent used to form the 7-substituent in a slight molar excess over Compound A (e.g., 33 mM vs. 30 mM) was added, and the resulting alkylating reaction mixture was stirred for a time period of about 16 hours at a temperature of about 20 to about 40 degrees C.

The solvent was thereafter removed in vacuo and the residue treated with distilled or deionized water (150 ml) and methylene chloride (150 ml). The solid obtained was filtered and recrystallized from an appropriate solvent to yield a 1-amino-7-substituted-8-oxo-guanosine, and complete "Step 1" of the usually used two-step synthesis procedure.

Step 2

The product of Step 1 was thereafter dissolved in concentrated HCl (e.g., 4.65 mM in 15 ml of HCl) to which aqueous sodium nitrite was added (e.g. 4.19 mM in 5 ml water) at zero degrees C., followed by stirring for about one hour. The resulting deaminated product was thereafter obtained by standard crystallization techniques unless otherwise noted.

The preparation of specific, exemplary compounds using the above two-step method and other methods are disclosed below, as are other syntheses.

EXAMPLE 2

7-Butyl-8-oxoguanosine (23644)

Following the two-step procedure of Example 1, using butyl iodide as the alkylating agent, the title compound was obtained in 15 percent overall yield as white powder, mp above 230° C. NMR (DMSO-$d_6$): δ 10.8 (bs,1H); 6.4(bs,2H); 5.6(d, J=5Hz, 1H). IR (KBr): 1680, 1610 and 1510 cm$^{-1}$.

Analysis Calculated for $C_{14}H_2N_5O_6$:
C, 47.32; H, 5.96; N,19.71;
Found: C, 47.03; H, 5.86; N, 19.56.

EXAMPLE 3

7-(2-Butenyl)-8-oxoguanosine (23679)

Following the two-step procedure of Example 1, using 2-butenyl bromide as the alkylating agent, the title compound was obtained in 10 percent overall yield as white powder, mp 167°-170°. NMR(DMSO-$d_6$): δ 10.7(bs, 1H); 6.4(bs, 2H); 5.4-5.6(bs, 3H); 3.3(bs, 3H). IR (KBr): 1690, 1650 1600 cm$^{-1}$.

Analysis calculated for $C_{14}H_{19}N_5O_6$·$H_2O$:
C, 45.28; H, 5.70; N, 18.86;
Found: C 45.16; H, 5.61; N, 18.82.

EXAMPLE 4

7-Hexyl-8-oxoguanosine (23924)

Following the two-step procedure of Example 1, using hexyl iodide as the alkylating agent, the title compound was obtained in 8% overall yield as beige powder, mp 196°-199° C. NMR (DMSO-$d_6$):δ 10.8(bs, 1H); 6.5(bs, 2H). IR (KBr):1680, 1640, and 1600 cm$^{-1}$.

Anal. Calculated for $C_{16}H_{25}N_5O_6$:
C, 50.12; H, 6.57; N, 18.27;
Found: C, 49.93; H, 6.52; N, 18.24.

EXAMPLE 5

7-Propyl-8-oxoguanosine (24069)

A mixture of 7-allyl-8-oxoguanosine (Example 8; 1.0 g, 2.9 mM) 10% Pd/C (100 mg) and ethanol (100 ml) was stirred at room temperature under an atmosphere of hydrogen for 3 hours. The catalyst was filtered through a pad of Celite and washed with ethanol (100 ml). The combined filtrate was concentrated in vacuo. The residue was dissolved in methanol (20 ml) and treated with ether (200 ml). The resulting solid was filtered and dried at 60° C. to provide the title compound in 55% yield as a white powder, mp 151°-153° C. NMR(DMSO-$d_6$):δ 10.8(bs,1H); 6.5(bs, 2H); 5.5(d J=5.5 Hz, 1H); 0.8(d, J=7 Hz, 3H). IR (KBr): 1680 and 1640 cm$^{-1}$.

Analysis calculated for $C_{13}H_{19}N_5O_6$:
C, 45.75; H, 5.61; N, 20.56;
Found: C, 45.41; H, 5.56; N, 20.09.

EXAMPLE 6

7-Ethyl-8-oxoguanosine (23643)

Following the two-step procedure of Example 1, using ethyl iodide as the alkylating agent, the title compound was obtained in 15 percent overall yield as white powder, mp 185°-187° C. NMR(DMSO-$d_6$): δ 6.7(bs; 2H); 5.7(d, J=5 Hz, 1 H); 1.2 (t, J=6 Hz, 3H). IR(KBr): 1680, 1640, 1610 and 1460 cm$^{-1}$.

Analysis calculated for $C_{12}H_{17}N_5O_6$·½$H_2O$:
C, 42.86; H, 5.39; N, 20.82;
Found: C, 43.17; H, 5.24; N, 20.45.

EXAMPLE 7

7-Decyl-8-oxoguanosine (23894)

Following the two-step procedure of Example 1, using decyl iodide as the alkylating agent, the title compound was obtained in 10 percent overall yield as a white powder, mp 174°-176° C. NMR(DMSO-$d_6$): δ 10.8(bs, 1 H); 6.4(bs, 2H); 5.6(d, J=5 Hz 1 H). IR(KBr): 1690, 1590 and 1450 cm$^{-1}$.

Analysis calculated for $C_{20}H_{33}N_5O_6$:
C, 54.66; H, 7,57; N, 15.93;
Found: C, 54.17; H, 7.44; N, 15.90.

EXAMPLE 8

7-(2-Propenyl)-8-oxoguanosine (21757) [Also, 7-Allyl-8-oxoguanosine]

Two procedures were utilized for the preparation of the title compound, that is also referred to herein as 7-allyl-8-oxoguanosine.

Procedure 1

Following the two-step procedure of Example 1 in which allyl bromide (3-bromopropene) was used as the alkylating agent, the title compound was prepared in a 40 percent yield from the corresponding 1-amino compound as a white powder, mp 230°-231° C. NMR (DMSO-$d_6$):δ 5.6 (d, J=5 Hz 1H); 6.5 (bs, 2H); 10.8 (bs, 1H). IR (KBr): 1660, 1590 and 1560 cm$^{-1}$.

Analysis calculated for $C_{13}H_{17}N_3O_6$:
C, 46.02; H, 5.05; N, 20.64;
Found: C, 45.63; H, 5.10; N, 20.56.

Procedure 2

A. Step 1: 8-(2-Propenyl)oxyguanosine

A mixture of 8-bromoguanosine (e.g., Sigma Chemical Co., St. Louis, Mo.; 10 g, 29.5 mM), sodium hydride (60% in oil, 5g, 125 mM), allyl alcohol (20 ml) and dimethylsulfoxide (DMSO: 200 ml) was heated at 60° C. under $N_2$ for 3 hours. The mixture was permitted to cool to about ambient room temperature, and was thereafter poured into diethyl ether (1 liter) to give a gray precipitate.

The ethereal layer was decanted and discarded. The solid residue was treated with water (50 ml) and acetic acid (10 ml). The solid was filtered and purified by reverse phase HPLC (C-18) to provide the 2-propenyl ether as a white powder in a 20 percent yield (1.8 g). NMR (DMSO-$d_6$): δ 6.3 (bs, 2H); 6.2-5.8 (m, 1H); 5.6 (d, J=5 Hz, 1H).

B. Step 2: 7-allyl-8-oxoguanosine

A mixture of 8-(2-propenyl)-oxyguanosine (40 mg, 0.12 mM) in water (50 ml) was heated at reflux for 3 hours. The reaction mixture was cooled to ambient room temperature, and the title compound was obtained by reverse phase HPLC (C-18) in 85 percent yield.

EXAMPLE 9

7-(2-Propenyl)-8-thioxoguanosine [Also, 7-allyl-8-thioxoguanosine](22444)

The title compound, also referred to herein as 7-allyl-8-thioxoguanosine and 7-allyl-8-mercaptoguanosine (7a8MGuo), was prepared using two different rearrangement procedures from 8-(2-propenylmercapto)-guanosine.

A. Step 1: 8-(2-propenylmercapto)guanosine (22300)

Allyl bromide (8g, 63.5 mM) was added to a mixture of 8-thioxoguanosine (20 g, 63.5 mM) and potassium carbonate (10 g, 72 mM) in DMF (300 ml), and the resulting mixture was heated with stirring at a temperature of 45° C. for 90 minutes.

The mixture was thereafter cooled to ambient room temperature and poured into a solution of diethyl ether (1.4l) and acetic acid (5 ml). The resulting solid was filtered and washed with water (250 ml), acetone (200 ml) and then diethyl ether, and then dried in an oven at 60° C. to provide the titled thioether (14.7 g, 67 percent yield) as a white powder, mp 225° C. (decomp.). NMR (DMSO-$d_6$): δ 5.70-5.91 (m, 2H); 6.38 (bs, 2H). IR (KBr): 1700, 1640 and 1610 cm$^{-1}$.

Analysis calculated for $C_{13}H_{17}N_5O_5S$:
C, 43.93; H, 4.82; N, 19.71;
Found: C, 44.10; H, 4.82; N, 19.69.

B. Rearrangement

Step 2: Procedure 1: 7-allyl-8-thioxoguanosine

Bistrimethylsilylacetamide (72 g, 354.7 mM) was added to a suspension of 8-(2-propenylmercapto)guanosine (20 g, 56.3 mM) as starting material in chloroform (500 ml), and the resulting mixture was heated at reflux for a period of 16 hours under $N_2$ After cooling, most of the solvent was removed in vacuo, and the residue was heated at 40° C. under vacuum for a period of 6 hours.

The oily residue was admixed with tetrahydrofuran (500 ml), PdCl$_2$ (10.3 g, 58.3 mM) and benzonitrile (12.1 g, 117 mM), and the resulting admixture was heated at reflux under $N_2$ for 3 hours. That admixture was thereafter cooled to ambient room temperature, further admixed with pyridine (25 ml) and stirred overnight (about 16 hours). The admixture was filtered through silica gel and washed with methylene chloride (2×300 ml). The combined filtrate was concentrated in vacuo, and the residue admixed with a mixture of water, methanol and acetic acid (500 ml; 10:10:1) and stirred for an additional time period of about 16 hours.

The majority of the added solvents was removed in vacuo, the residue was dissolved in DMF (1 liter), and then treated with charcoal. The suspension so obtained was filtered through a bed of Celite, and the filtrate concentrated in vacuo. The residue was treated with methanol and the resulting solid filtered, washed with acetone, and dried in an oven at 60° C. to provide 7-allyl-8-thioxoguanosine (8.5 g, 42.5 percent yield) as an off-white powder, mp above 230° C. NMR (DMSO-$d_6$): δ 5.90 (m, 1H); 6.32 (d, J=5 Hz 1H); 6.56 (bs, 2H); 10.60 (bs, 1H). IR (KBr): 1700, 1635, 1605 and 1450 cm$^{-1}$.

Analysis calculated for $C_{13}H_{17}N_5O_5S$:
C, 43.93; H, 4.82; N, 19.71;
Found: C, 43.96; H, 4.87; N, 19.62.

Step 2: Procedure 2: 7-allyl-8-thioxoguanosine

A solution containing 8-(2-propenylmercapto)guanosine (60 g) as starting material in DMF (60 g) was heated at a bath temperature of 130° C. under $N_2$ for a period of 9 days. The resulting reaction mixture was cooled to ambient room temperature and the solvent was removed in vacuo. The residue was treated with methanol. The resulting solid was filtered and washed with acetone, and then dried in an oven at 60° C. to provide the title compound (21 g, 36 percent yield) as an off-white powder.

EXAMPLE 10

7-(2-Propenyl)-8-selenoxoguanosine (23369)

The title compound, also called 7-allyl-8-selenoxoguanosine herein, was prepared by reacting 8-selenoxoguanosine [Chu et al., *J. Med. Chem.*, 18:559–564 (1975)] and allyl bromide as described in Example 9 followed by thermal rearrangement. The product was recrystallized from water and dried, mp 227°–230° C.

Analysis calculated for $C_{13}H_{17}N_5O_5Se$:
C, 38.28; H, 4.26; N, 17.41;
Found: C, 38.77; H, 4.25; N, 16.92.

EXAMPLE 11

7-[(3-Phenyl)-2-propenyl]-8-oxoguanosine (also, 7-cinnamyl-8-oxoguanosine) (22827)

The title compound was prepared from the corresponding 1-amino derivative following the general two-step procedure of Example 1. In Step 2, to a solution of that 1-amino-7-[(3-phenyl)-2-propenyl]-8-oxoguanosine (2 g, 4.65 mM) in concentrated HCl (15 ml) was added sodium nitrite (0.29 g, 4.19 mM) in water (5 ml) at zero degrees. The resulting mixture was stirred for one hour. Most of the solvent was removed in vacuo to provide a pale yellow solid. That solid was triturated with methanol to provide the title compound as a white powder (65 percent yield), mp 240° C. NMR (DMSO-$d_6$): δ 10.8 (bs, 1H); 5.6 (d, J=5 Hz 1H). IR (KBr): 1680, 1610 and 1530 cm$^{-1}$.

Analysis calculated for $C_{19}H_{21}N_5O_6$:
C, 54.94; H, 5.10; N, 16.86;
Found: C, 54.70; H, 5.10; N, 16.90.

EXAMPLE 12

8-Cyanoimino-7-(2-propenyl)guanosine (24328)

To a solution of 7-(2-propenyl)-8-thioxoguanosine (Example 9; 10 g, 28.2 mM) in DMSO (200 ml) was added methyl iodide (6 g, 42.3 mM) at room temperature under nitrogen, and the resulting admixture was stirred for 3 hours. The mixture was cooled to zero degrees C. and cyanamide (2.4 g. 56.5 mM) was added, followed by sodium hydride (60% oil dispersion, 1.79 g, 44.8 mM). The resulting mixture was allowed to warm to ambient room temperature, and was stirred for 1 hour.

The mixture was poured into diethyl ether (1.4 l), and stirred for 10 minutes. The organic layer was decanted, and the residue was further treated with diethyl ether (1.4 l) and acetic acid (50 ml). The organic layer was decanted and residue dissolved in water (500 ml).

The water layer was purified by reverse phase (C-18) HPLC to give the title compound in 35% yield as white powder, mp 194°–197° C. NMR (DMSO-d$_6$): δ 11.0 (bs, 1H); 6.5(bs, 2H), 5.5 (d, J=5 Hz 1H). IR (KBr): 2190, 1700 and 1640 cm$^{-1}$.

Analysis calculated for C$_{14}$H$_{17}$N$_7$O$_5$·½ H$_2$O:
C, 45.16; H, 4.87; N, 26.33;
Found: C, 45.00; H, 4.66; N, 26,07.

EXAMPLE 13

8-(2-Butenylmercapto)guanosine (22435)

Following the first procedure for the preparation of 8-(2-propenylmercapto)guanosine (Example 9), but substituting 2-butenyl chloride for allyl bromide, the title compound was obtained in 48 percent yield as a white powder, mp 210° C. (decomp.). NMR (DMSO-d$_6$): δ 6.3 (bs, 2H); 5.6 (d, J=5 Hz 1H); 1.6 (d, J=6 Hz 3H). IR (KBr): 1690, 1630, 1600, 1510 and 1365 cm$^{-1}$.

Analysis calculated for C$_{14}$H$_{19}$N$_5$O$_5$S:
C, 45.52; H, 5.18; N, 18.96;
Found: C, 45.38; H, 5.32; N, 18.79

EXAMPLE 14

8-(Cinnamylmercapto)guanosine (22359)

Following the procedure for the preparation of 8-(2-propenylmercapto)guanosine (Example 9A), but title compound was obtained in 33 percent yield as an off-white powder, mp 172° C. (decomp.). NMR (DMSO-d$_6$): δ 7.25 (br, 5H); 6.7–6.2 (m, 4H); 5.7 (d, J=5 Hz 1H). IR (KBr): 1690, 1640 and 1600 cm$^{-1}$.

Analysis calculated for C$_{19}$H$_{21}$N$_5$O$_5$S:
C, 52.89; H, 2.91; N, 16.23;
Found: C, 53.26; H, 4.90; N, 16.08.

EXAMPLE 15

7-(2-Propenyl)-8-thioxo-2′,3′-O-isopropylidineguanosine hemihydrate (23083)

A mixture of 7-(2-propenyl)-8-thioxoguanosine (Example 9; 6 g, 16.9 mM), 2,2-dimethoxypropane (5 ml, 40.7 mM), acetone (200 ml) and concentrated sulfuric acid (10 drops) was stirred under N$_2$ at ambient room temperature for a time period of 52 hours. The mixture was cooled to zero degrees C. and treated with concentrated ammonium hydroxide (5 ml). Most of the solvent was removed in vacuo, and the white solid was filtered. The solid was washed with water, then acetone, and thereafter diethyl ether, and then dried in an oven at 60° C. to provide the title compound as a pale yellow powder in 75 percent yield mp 237° C. (decomp.). NMR (DMSO-d$_6$) δ 1.32 (s, 3H); 1.52 (s, 3H); 5.92 (m, 1H); 6.58 (bs, 1H), 6.95 (bs, 2H). IR (KBr): 1695, 1630, 1600 and 1450 cm$^{-1}$.

Analysis calculated for C$_{16}$H$_{21}$N$_3$O$_3$S·½ H$_2$O:
C, 47.51; H, 5.48; N, 17.32;
Found: C, 47.08; H, 5.12; N, 17.30.

EXAMPLE 16

7-Cinnanmyl-2′,3′-isopropylidene-8-oxoguanosine hemihydrate (23803)

Following the procedure of Example 15, but substituting 7-cinnamyl-8-oxoguanosine (Example 11) for 7-(2-propenyl)-8-thioxoguanosine, the title compound was obtained in 35 percent yield as off-white powder, mp 230° C. NMR(DMSO-d$_6$): δ 10.9(bs, 1H); 7.3-7.6 (m,5H); 6.6(bs, 2H), 6.4(m, 2H). IR (KBr): 1680, 1630, 1590, 1450, 1420 and 1380 cm$^{-1}$.

Analysis calculated for C$_{22}$H$_{25}$N$_5$O$_6$·½H$_2$O):
C, 56.89; H,5.64; N,15.07;
Found: C, 57.08; H,5.53; N,15.12.

EXAMPLE 17

8-Cyanoimino-7-(2-propenyl)-2′,3′-O-isopropylideneguanosine hemihydrate (24456)

Following the procedure of Example 12, but substituting 7-(2-propenyl)-8-thioxo-2′,3′-O-isopropylideneguanosine (Example 15) for 7-(2-propenyl)-8-thioxoguanosine, the title compound was obtained in 51 percent yield as a light brown powder, mp 222° C. (decomp.). NMR (DMSO-d$_6$): δ 7.45(bs, 1H); 6.9 (bs, 2H); 6.2 (bs, 1H); 1.5 and 1.3 (both s, 3H each). IR (KBr): 2185 and 1595 cm$^{-1}$.

Analysis calculated for C$_{17}$H$_{21}$N$_7$O$_5$·½H$_2$O:
C, 49.51; H, 5.38; N, 23.79;
Found: C, 49.34; H, 5.22; N, 23.06.

EXAMPLE 18

5′-Acetyl-7-(2-propenyl)-2′,3′-O-isopropylidene-8-thioxoguanosine (23287)

A mixture of 7-(2-propenyl)-2′3′-O-isopropylidene-8-thioxoguanosine (Example 15; 1.2 g, 3 mM), triethylamine (3 ml), acetic anhydride (0.3 g, 2.9 mM) and methylene chloride (100 ml) was stirred at ambient room temperature for a period of 16 hours. The mixture was poured into water (100 ml), the organic layer separated, and the aqueous layer was extracted with methylene chloride (2×50 ml).

The combined organic layer was dried (Na$_2$SO$_4$), and the solvent removed in vacuo. The residue was purified by column chromatography on silica gel [100 g, ethyl acetate/hexane (9:1 v/v)] to provide the title compound as an off-white powder (950 mg) in 70 percent yield, mp 179° C. (decomp.). NMR (DMSO-d$_6$): δ 11.1 (bs, 1H); 6.85 (bs, 2H); 6.6 (s, 1H); 2.01 (s, 3H); 1.45 and 1.32 (both s, 3H each). IR (KBr): 1730, 1710, 1680 and 1630 cm$^{-1}$.

Analysis calculated for C$_{18}$H$_{23}$N$_5$O$_6$S:
C, 49.42; H, 5.30; N, 16.01;
Found: C, 49.33; H, 5.36; N, 15.50.

EXAMPLE 19

7-(2-Propenyl)-6,5′-dibenzoyl-2′,3′-O-isopropylidene-8-thioxoguanosine (22314)

Following the general procedure of Example 18, but substituting benzoyl chloride for acetic anhydride, the title compound was obtained as a yellow powder in 12 percent yield, mp 99°–101° C. NMR (CDCl$_3$): δ 8.3-7.4 (m, 10H), 6.85 (d, J=1Hz, 1H); 1.61 and 1.38 (both s, 3H each). IR (KBr): 1760, 1720, 1640, 1600 and 1450 cm$^{-1}$.

Analysis calculated for C$_{30}$H$_{29}$N$_5$O$_7$S:
C, 59.69; H, 4.84; N, 11.60;
Found: C, 59.73; H, 4.88; N, 11.49.

EXAMPLE 20

7-(2-Propenyl)-2-N,5′-O-dibenzoyl-2′,3′-O-isopropylidene-8-thioxoguanosine hemihydrate (23350)

Continued elution of the silica gel column used for purification in Example 19 with the ethyl acetate/hexane (3:7 v/v) provided the title compound as a pale yellow powder in 20 percent yield, mp 134°-136° C. NMR (CDCl₃): δ 10.1 (bs, 1H); 8.2-7.3 (m, 10H); 1.65 and 1.34 (both s, 3H each). IR (KBr): 1710, 1680, 1610 and 1588 cm⁻¹.

Analysis calculated for $C_{30}H_{29}N_5O_7S\cdot\frac{1}{2}H_2O$:
C, 58.81; H, 4.94; N, 11.43;
Found: C, 58.77; H, 4.82; N, 11.50.

EXAMPLE 21

7-(2-Propenyl)-5'-benzoyl-2',3'-O-isopropylideneguanosine-8-thioxoguanosine quarterhydrate (23351)

Still further elution of the silica gel column used in Examples 19 and 20 with ethyl acetate/hexane (4:1 v/v) provided the title compound as a pale yellow powder in 21 percent yield, mp 214° C. (decomp.). NMR (DMSO-d₆): δ 11.1 (bs, 1H); 7.9-7.3 (m, 5H); 6.7 (bs, 2H); 6.6 (s, 1H); 1.6 and 1.4 (both s, 3H each). IR (KBr): 1700; 1630, 1590 and 1450 cm⁻¹.

Analysis calculated for $C_{23}H_{25}N_5O_6\cdot 1/4H_2O$:
C, 54.80; H, 5.10; N, 13.90;
Found: C, 54.77; H, 4.99; N, 13.85.

EXAMPLE 22

7-(2-Propenyl)-8-thioxo-2',3',5'-triacetylguanosine (22360)

To a mixture of 7-(2-propenyl)-8thioxoguanosine (7a8MGuo; 1 g, 2.8 mM), triethylamine (2 ml), acetic anhydride (1.2 ml, 13 mM) and methylene chloride (50 ml) was added 4-N,N-dimethylamino-pyridine (10 mg). The resulting reaction mixture was stirred under N₂ for 16 hours at room temperature.

Further methylene chloride (50 ml) was added and the solution was washed with 1N HCl, brine and then water, and it was thereafter dried (Na₂SO₄). The solvent was removed in vacuo, and the residue was purified by column chromatography on silica gel (200 g) using ethyl acetate as eluant. The title compound was obtained as a pale yellow powder in 54 percent yield, mp 100°-102° C. NMR (CDCl₃): δ 2.01 (s, 3H); 2.10 (s, 6H); 6.79 (d, J=3 Hz 1H). IR (KBr): 1740, 1690, 1630, 1450 and 1230 cm⁻¹.

Analysis calculated for $C_{19}H_{23}N_5O_8S$:
C, 47.39; H, 4.82; N, 14.55;
Found: C, 47.29; H, 4.84; N, 14.19.

A second, larger scale preparation of the title compound provided that compound in 26 percent yield, and also 7-(2-propenyl)-8-thioxo-2',3'5', 2-N-tetraacetylguanosine (25177) in a 40 percent yield, mp 90°-92°. NMR (DMSO-d₆): δ 12.1 (bs, 1H); 11.4 (s, 1H); 6.4 (d, J=5 Hz 1H); 2.15, 2.00, 1.94 and 1.90 (each s, 3H each). IR (KBr): 1750 and 1690 cm⁻¹.

Analysis calculated for $C_{21}H_{25}N_5O_9S$:
C, 48.18; H, 4.81; N, 13.38;
Found: C, 48.20; H, 4.69; N, 13.32.

EXAMPLE 23

7-Benzyl-8-oxoguanosine (24234)

Following the two-step procedure of Example 1, in which benzyl bromide was used as the alkylating agent, the title compound was obtained in 20% overall yield as an off-white powder, mp 175° C. DMSO-d₆): 10.7 (bs,1H), 7.3 (s,5H), 6.4 (bs, 2H), 5.6 (d, J=5 Hz 1H). IR (KBr): 1680, 1600 and 1450 cm⁻¹.

Analysis calculated for $C_{17}H_{19}N_5O_6$:
C, 52.44; H, 4.92: N 17.99;
Found: C, 52.47; H 5.03; N, 17.10.

B. Exemplary Compositions For Administration

Exemplary solid and liquid compositions suitable for administering the compounds of the present invention are described below using five of the more preferred guanine nucleoside derivatives as exemplary active ingredients.

|  | Parts by Weight |
|---|---|
| 7-Allyl-8-oxoguanosine | 2.5 |
| Lactose, powdered | 36.4 |
| Corn starch, dry | 34.5 |
| Finely divided SiO₂ | 5.6 |
| Polyvinylpyrrolidone | 0.6 |
| Magnesium stearate | 0.4 |
|  | 80.0 |

The guanosine derivative is thoroughly admixed with the lactose, 25.0 parts by weight of the corn starch, and 4.0 parts by weight of the SiO₂. The resulting admixture is then uniformly moistened with a 5% ethanolic solution of polyvinylpyrrolidone. The moist mass is then passed through a one-millimeter mesh screen to produce a granulate. The resultant granulate is dried for about 24 hours at 60° C. in a drying chamber. The dried granulate is again passed through a one-millimeter mesh screen. 70.0 Parts of the obtained granulate are admixed in a suitable mixer with a mixture consisting of the remainder of the SiO₂, the remainder of the corn starch and all of the magnesium stearate, which mixture previously had been passed through a one-millimeter mesh screen. The thus-obtained admixture is then pressed into tablets weighing 800 milligrams each and containing 25 milligrams of the guanosine.

Starch Capsules

Capsule contents are compounded from the following ingredients:

|  | Parts by Weight |
|---|---|
| 7-Butyl-8-oxoguanosine | 10.0 |
| Lactose | 450.0 |
| Corn Starch | 540.0 |
|  | 1000.0 |

The guanosine derivative is gradually admixed with the lactose. When all of the lactose has been admixed, the obtained admixture is blended with the corn starch. The resulting blend is then filled into capsules holding 1.0 gram of the blend. Each capsule contains 10 milligrams of the guanosine derivative.

| 7-(2-Butenyl)-8-oxoguanosine | 500 grams |
|---|---|
| Dicalcium Phosphate | 1000 grams |
| Methyl cellulose, U.S.P. (15 cps) | 75 grams |
| Talc | 150 grams |
| Corn Starch | 250 grams |
| Magnesium stearate | 25 grams |
|  | 2000 grams |

The guanosine derivative and dicalcium phosphate are mixed well, granulated with 7.5 percent solution of methyl cellulose in water, passed through a No. 8 screen (U.S. Standard Sieve Series) and dried carefully. The dried granules are passed through a No. 12 screen (U.S. Std. Sieve Series), mixed thoroughly with the talc, starch and magnesium stearate, and compressed into tablets.

Injectable Preparation

A sterile preparation suitable for intramuscular, subcutaneous or intracavitary injection and containing 50 milligrams of 7-benzyl-8-oxoguanosine in each milliliter of ingredients is prepared from the following types and amounts of ingredients:

| 7-benzyl-8-oxoguanosine | 5 grams |
| --- | --- |
| Physiological saline | 98 milliliters |
| sesame oil | 2 milliliters |

The guanosine derivative and saline are admixed and sonicated for a period of time sufficient to provide a substantially homogenous dispersion. The sesame oil is thereafter admixed and the new admixture is similarly homogenized to provide an emulsion. After emulsification, five to fifteen percent of the final volume of this sterile preparation are injected subcutaneously or intraperitoneally once or twice a week to enhance immunity.

Aqueous Preparation for Oral Use

An aqueous preparation for oral use containing in each 5 milliliters (1 teaspoon) 25 milligrams of 7-propyl-8-oxoguanosine is prepared from the following ingredients:

| 7-Propyl-8-oxoguanosine | 5.0 grams |
| --- | --- |
| Methylparaben, U.S.P. | 0.75 grams |
| Propylparaben, U.S.P. | 0.25 grams |
| Saccharin sodium | 1.25 grams |
| Cyclamate sodium | 0.25 grams |
| Glycerin | 300 milliliters |
| Tragacanth powder | 1.0 grams |
| Orange oil flavor | 1.0 grams |
| F.D. and C. orange dye | 0.75 grams |
| Deionized water | q.s. to 1000 milliliters |

C. Methods

Lymphocyte cultures. The serum-containing culture medium water prepared to contain the following per 100 milliliters: 91.9 milliliters RPMI 1640 (Flow Laboratories, Inc., Rockville, Md.), 0.1 milliliters of $100 \times$ glutamine, 1.0 milliliter of $100 \times$ sodium pyruvate, 1 0 milliliter of $50 \times$ nonessential amino acids, 1.0 milliliter of water containing $10^4$ units of penicillin G and $10^4$ micrograms of streptomycin, and 5.0 milliliters of a supportive lot of fetal calf serum (FCS). These ingredients were admixed to apparent homogeneity. Spleen cell suspensions and populations enriched for splenic B cells were prepared as described in Goodman et al., *J. Immunol.*, 121:1905 (1978).

For evaluation of the primary humoral immune response to sheep erythrocytes (SRBC), $5 \times 10^6$ to $10^7$ murine spleen cells were cultured in 1.0 milliliter of 5% FCS-containing medium for 4 or 5 days in the presence and absence of immunogen. Cells were incubated in culture trays (Costar, Cambridge, Mass.) at 37° C. in a humidified atmosphere of 10% $CO_2$ in air using tissue culture boxes (CBS Scientific, Del Mar, Calif.) that were rocked at a frequency of 7 cycles per minute. Pooled SRBC are available from the Colorado Serum Co., Denver Colo.

Human peripheral blood lymphocytes (PBL) were prepared from normal heparinized venous blood by Ficoll-diatrizoate density gradient centrifugation. PBL were depleted of suppressor T cells bearing the histamine type 2 receptor by adhering them to the surfaces of histamine-rabbit serum albumin-coated plastic petri dishes (Cell-ect No. 2 kit; Seragen, Boston, Mass.) and by recovering the nonadherent cells by panning as described by Wysocki and Sato, *Proc. Natl. Acad. Sci. USA*, 75:2844 (1978) and modified by Cavagnaro and Osband, *Biotechniques*, January/February:30 (1983).

The tissue culture medium employed in these studies for human lymphocytes was prepared as follows: One hundred milliliters (ml) contained 87.9 ml RPMI 1640 (Flow Laboratories, Rockville, Md.), 0.1 ml $100 \times$ glutamine, 1.0 ml of 1.0 M HEPES buffer (Microbilogical Associates, Betheseda, Md.), 1.0 ml of water containing $10^4 U$ of penicillin G and $10^4$ micrograms of streptomycin, and 10 ml of fresh autologous heat-inactivated plasma. For evaluation of the primary humoral immune response to SRBC, lymphoid cells prepared as above were cultured at a density of $2 \times 10^6$/ml in a volume of 1.0 ml containing $5 \times 10^6$ SRBC as antigen (Colorado Serum Co., Denver, Colo.) together with IL-2 (a partially purified preparation of human IL-2 that was free of interferon-gamma activity was obtained from Electro-Nucleonics, Inc., Silver Spring, Md.) and the guanine nucleoside derivative.

Assay of plaque forming cells (PFC). PFC secreting antibodies against SRBC were evaluated after 4 or 5 days of culture using a modification of the hemolytic plaque assay of Jerne and Nordin, *Science*, 140:405 (1963). The cells were brought up in complete medium before plaquing; they were plaqued in standard low $M_r$ agarose (Bio-Rad Laboratories, Richmond Calif.), and were incubated in SRBC-absorbed guinea pig complement for one hour after a 1.5 hour incubation without complement.

T Cell Replacing Activity. $5 \times 10^6$ Viable CBA/CaJ mouse B cells were cultured. As discussed in greater detail hereinafter, these cells were generated by sequentially treating spleen cells first with complement-fixing monoclonal antibodies directed against thy 1.2 antigens of T cells and second with complement to lyse any T cells present (New England Nuclear, Boston, Mass.). The cells so treated were thereafter grown with or without 0.1 ml of 0.1 percent (v/v) SRBC as immunogen in serum-containing media further containing incremental amounts of a guanosine derivative ranging in amount from zero through $10^4$ molar. Direct PFC to SRBC are determined 4 days thereafter Mice CBA/CaJ mice, 8–16 weeks of age, are purchased from the Jackson Laboratory, Bar Harbor, Me. A breeding nucleus of CBA/N mice was provided by the Animal Production Section, National Institutes of Health, Bethesda, Md.. SJL, BDF/ and C57BL/6J mice 8–16 weeks old were obtained from the mouse breeding facility at the Scripps Clinic and Research Foundation, La Jolla, Calif. All mice were maintained on Wayne Lab Blox F6 pellets (Allied Mills, Inc., Chicago, Ill.) and chlorinated water acidified with HCl to a pH value of 3.0.

Cell preparations. Spleen and thymus cell suspensions were prepared as described in Goodman et al., *J. Immunol.*, 121:1905 (1978). B cell-enriched populations were prepared by treating $10^8$ spleen cells with a 1:1000 dilution of monoclonal anti-Thy 1.2 antibody (New England Nuclear, Boston, Mass.) for 30 minutes at 4° C. Treated cells were centrifuged at $280 \times$ gravity for 10 minutes, antibodies were removed, and the cells were resuspended in a 1:6 dilution of CBA RBC-absorbed guinea pig complement at 37° C. for 45 minutes. Cells were then washed and cultured as described before.

Injections. Mice were injected i.p. with a solution containing 50 ug of TNP-BSA. Within, about 30 minutes of the immunizing injection, the two groups of six mice also received 0.2 ml i.p. injections 7a8MGuo in 100 percent sesame oil, or 2 percent (v/v) sesame oil sonicated in normal saline, with the 7a8MGuo being present at 5 mg/ml. A third group of six mice received the immunization but no guanosine derivative. Anti-TNP-BSA antibody titers were determined using standard techniques.

T Helper Cell Activation. $1.5 \times 10^5$ viable spleen cells from SJL mice or CBA/CaJ mouse thymocytes were cultured with or without an equal number of irradiated (2500 rads) spleen cells from CBA/CaJ or BDF$_I$ mice respectively, in 0.2 ml of culture medium in the presence of incremental concentrations of the exemplary 7,8-disubstituted guanine derivatives. The lymphocyte culture medium utilized was that described before, and was further supplemented with 2-mercaptoethanol to a final concentration of 50 uM. Thymocyte cultures also contained 10 percent (v/v) of a concanavalin A-conditioned rat spleen cell medium sold under the name Rat T Cell Monoclone by Collaborative Research. Following 90 hours of culture, one microCurie [$^3$H]TdR per culture was admixed, and the resulting culture was maintained for a further six hour time period.

The cultures were harvested with a Brandel cell harvester (M24V, Biological Research and Development Laboratories, Rockville, Md.) onto glass fiber filter disks. Filter disks were transferred to plastic scintillation vials, covered with liquid scintillation cocktail, and counted in a Beckman LS5700 liquid scintillation counter.

The present invention has been described with respect to preferred embodiments. It will be clear to those skilled in the art that modifications and/or variations of the disclosed subject matter can be made without departing from the scope of the invention set forth herein.

What is claimed is:

1. A substituted guanine nucleoside derivative that corresponds to the formula

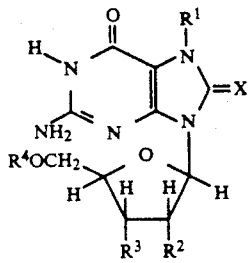

wherein X is O, S, Se or NCN;
$R^1$ is a straight, cyclic or branch chained hydrocarbyl radical having a length greater than an ethyl group and less than a decyl group;
$R^2$ and $R^3$ are the same or different radicals selected from the group consisting of hydrogen, hydroxyl, lower alkoxy, lower alkanoyloxy, and benzoxy or $R^2$ and $R^3$ together constitute a lower alkylidenedioxy radical;
$R^4$ is a radical selected from the group consisting of hydrogen, lower alkanoyl, and benzoyl; and
the pharmaceutically acceptable, non-toxic base addition salts thereof.

2. The substituted guanine nucleoside derivative of claim 1 wherein said $R^1$ radical is a straight chain radical selected from the group consisting of straight chain $C_3$–$C_6$ alkyl, a straight chain $C_3$–$C_6$ beta-alkenyl and a benzyl radical.

3. The substituted guanine nucleoside derivative of claim 1 wherein said $R^1$ radical is selected from the group consisting of propyl, butyl, allyl, 2-butenyl and benzyl, and X is O.

4. The substituted guanine nucleoside of claim 3 wherein $R^4$ is hydrogen.

5. The substituted guanine nucleoside derivative of claim 1 wherein $R^2$ and $R^3$ are hydroxyl, and $R^4$ is hydrogen.

6. A substituted guanine nucleoside derivative that corresponds to the formula

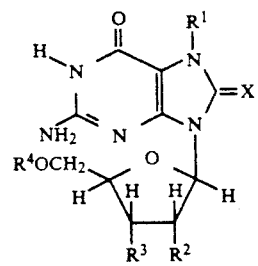

wherein X is O or S;
$R^1$ is a radical selected from the group consisting of propyl, allyl, butyl, 2-butenyl and benzyl;
$R^2$ and $R^3$ are the same or different radicals selected from the group consisting of hydroxyl, acetoxy, and benzoxy, or $R^2$ and $R^3$ together constitute an isopropylidenedioxy radical;
$R^4$ is a radical selected from the group consisting of hydrogen, acetyl and benzoyl; and
the pharmaceutically acceptable, non-toxic base addition salts thereof.

7. The substituted guanine nucleoside derivative of claim 6 wherein $R^1$ is allyl, and $R^2$ and $R^3$ are each an acetoxy radical.

8. The substituted guanine nucleoside derivative of claim 6 wherein $R^2$ and $R^3$ are hydroxyl and $R^4$ is hydrogen.

9. 7-Allyl-8-thioxo-2',3',5'-triacetylguanosine.

10. 7-Allyl-8-oxoguanosine.

11. 7-Butyl-8-oxoguanosine.

12. 7-(2-Butenyl)-8-oxoguanosine.

13. 7-Allyl-8-thioxoguanosine.

14. 7-Benzyl-8-oxoguanosine.

15. 7-Propyl-8-oxoguanosine.

16. A composition comprising a diluent amount of physiologically tolerable carrier admixed with an immunopotentiating effective amount of an immune response-enhancing substituted guanine nucleoside derivative, said substituted guanine having the formula

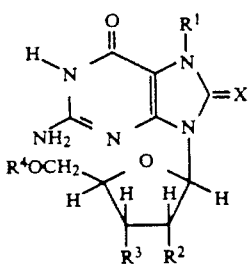

wherein X is O, S, Se or NCN;

$R^1$ is a straight, cyclic or branch chain hydrocarbyl radical having a length greater than an ethyl group and less than a decyl group;

$R^2$ and $R^3$ are the same or different radicals selected from the group consisting of hydroxyl, lower alkoxy, lower alkanoyloxy and benzoxy, or $R^2$ and $R^3$ together constitute a lower alkylidenedioxy radical;

$R^4$ is a radical selected from the group consisting of hydrogen, lower alkanoyl, and benzoyl; and the pharmaceutically acceptable, non-toxic base addition salts thereof.

17. The composition of claim 16 wherein said hydrocarbyl radical is a straight chain radical selected from the group consisting of a straight chain $C_3$-$C_6$ alkyl, a straight chain $C_3$-$C_6$ beta-alkenyl and a benzyl radical.

18. The composition of claim 16 wherein said $R^1$ radical is selected from the group consisting of propyl, butyl, allyl, 2-butenyl and benzyl, and X is O.

19. The composition of claim 16 wherein $R^2$ and $R^3$ are hydroxyl, and $R^4$ is hydrogen.

20. The composition of claim 16 wherein X is O or S.

21. A method of enhancing an immune response which comprises contacting leukocytes in an aqueous medium with a composition containing a diluent amount of a physiologically tolerable carrier admixed with an immunopotentiating effective amount of a substituted guanine nucleoside derivative, said substituted guanine nucleoside derivative having a structure that corresponds to the formula

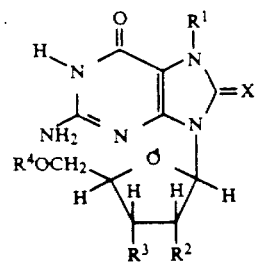

wherein X is O, S, Se or NCN;

$R^1$ is a straight, cyclic or branch chain hydrocarbyl radical having a length greater than an ethyl group and less than a decyl group;

$R^2$ and $R^3$ are the same or different radicals selected from the group consisting of hydrogen, hydroxyl, lower alkoxy, lower alkanoyloxy, and benzoxy or $R^2$ and $R^3$ together constitute a lower alkylidenedioxy radical;

$R^4$ is a radical selected from the group consisting of hydrogen, lower alkanoyl, and benzoyl; and the pharmaceutically acceptable, non-toxic base addition salts thereof.

22. The method of claim 21 wherein said cells are contacted in vitro in a culture medium.

23. The method of claim 22 wherein said potentiating effective amount is an amount sufficient to provide a concentration of about $1 \times 10^{-6}$ to about $3 \times 10^{-4}$ molar to about $10^6$-$10^7$ cells in one milliliter of culture medium.

24. The method of claim 21 wherein the cells contacted include B cells.

25. The method of claim 24 wherein said immune response is an antigen-specific response.

26. The method of claim 25 wherein said B cells are human B cells.

27. The method of claim 21 wherein said cells are T cells.

28. The method of claim 21 wherein said cells are neutrophils.

29. The method of claim 21 wherein said contacting is carried out in vivo by administering a unit dose of said composition to a mammal.

* * * * *

UNITED STATES PATENT AND TRADEMARK OFFICE
CERTIFICATE OF CORRECTION

PATENT NO. : 5,011,828

DATED : April 30, 1991

INVENTOR(S) : Michael Goodman et al.

It is certified that error appears in the above-identified patent and that said Letters Patent is hereby corrected as shown below:

Column 1, after the title and before the heading "CROSS-REFERENCE TO COPENDING APPLICATION", insert the following paragraph:

--This invention was made with government support under Contract Nos. AI 15284 and AI 07007 awarded by the National Institutes of Health. The government has certain rights in the invention.--

Signed and Sealed this

Eighth Day of February, 1994

*Attest:*

BRUCE LEHMAN

*Attesting Officer*     *Commissioner of Patents and Trademarks*